United States Patent

Daehne et al.

[11] 4,060,606
[45] Nov. 29, 1977

[54] 16-ETHERS OF FUSIDIC ACID DERIVATIVES

[75] Inventors: Welf von Daehne, Rungsted Kyst; Poul Rodbroe Rasmussen, Frederikssund, both of Denmark

[73] Assignee: Leo Pharmaceutical Products Ltd. A/S, Ballerup, Denmark

[21] Appl. No.: 693,976

[22] Filed: June 8, 1976

[51] Int. Cl.² .......................... A61K 31/56; C07J 7/00
[52] U.S. Cl. ................................ 424/238; 260/397.1; 424/181; 424/243
[58] Field of Search .................... 260/397.1; 424/238, 424/243

[56] References Cited

U.S. PATENT DOCUMENTS

| | | | |
|---|---|---|---|
| 2,937,118 | 5/1960 | Harthausen et al. | 167/65 |
| 3,117,059 | 1/1964 | Rubbstein | 167/65 |

FOREIGN PATENT DOCUMENTS

| | | | |
|---|---|---|---|
| 992,276 | 8/1962 | United Kingdom | 260/397.1 |

*Primary Examiner*—Elbert L. Roberts
*Attorney, Agent, or Firm*—Cushman, Darby & Cushman

[57] ABSTRACT

The present invention relates to a new series of fusidic acid derivatives, to salts and easily hydrolysable esters thereof, to the preparation of these compounds, and to pharmaceutical compositions containing the compounds. The new compounds have the general formula

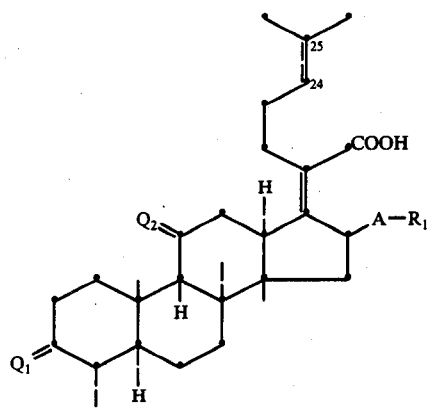

in which the $C_{24-25}$ bond is a single or a double bond, and in which $Q_1$ and $Q_2$ stand for

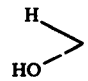

or oxygen; A stands for oxygen, sulphur or a sulfinyl radical; $R_1$ stands for a straight or branched alkyl radical having from 1 to 8 carbon atoms, an alkenyl or alkynyl radical having from 2 to 6 carbon atoms, a cycloalkyl radical having from 3 to 7 carbon atoms in the alicyclic ring, an aryl or aralkyl radical, a heterocyclic radical having 5 or 6 ring atoms, and containing oxygen, sulphur or nitrogen atoms, and pharmaceutically acceptable salts and easily hydrolysable esters thereof.

The compound of the present invention show interesting antimicrobial and pharmacokinetic properties. Thereby the compounds of the invention can be used in the treatment of bacterial infections in humans and animals.

46 Claims, No Drawings

16-ETHERS OF FUSIDIC ACID DERIVATIVES

The present invention relates to a new series of fusidic acid derivatives, to salts and easily hydrolyzable esters thereof, to the preparation of these compounds, and to pharmaceutical compositions containing the compounds. The new compounds have the general formula:

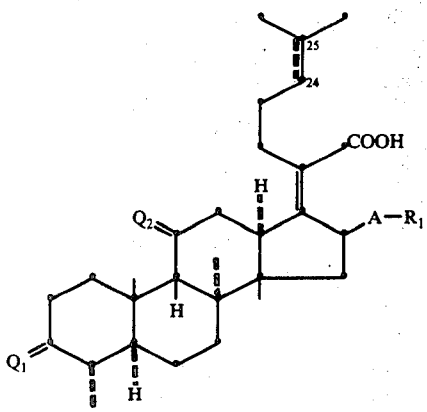

in which $Q_1$ and $Q_2$ stand for the group

or oxygen, A represents oxygen or sulphur or a sulphinyl radical, and $R_1$ stands for a straight or branched alkyl radical having from 1 to 8 carbon atoms, such as methyl, ethyl, propyl, isopropyl, butyl, isobutyl, tert.butyl, the known isomers of pentyl, hexyl, heptyl and octyl, such alkyl radicals being optionally substituted with halogen atoms or hydroxy, alkyloxy, aralkyloxy, aryloxy, alkanoyloxy, aralkanoyloxy, aroyloxy, sulfhydryl, alkylthio, aralkyltho, arylthio, alkanoylthio, aroylthio, azido, nitro, cyano, thiocyano, hydroxycarbonyl, alkyloxycarbonyl, aryloxycarbonyl, amino, alkylamino, dialkylamino, arylamino, alkanoylamino, and aroylamino groups; $R_1$ can further be an alkenyl or alkynyl radical having from 2 to 6 carbon atoms, such as allyl, crotyl or propargyl, a cycloalkyl radical having from 3 to 7 carbon atoms in the alicyclic ring, such as cyclopropyl, cyclobutyl, cyclopentyl, cyclohexyl, cycloheptyl, or the mono- or dihalo, lower alkyl, lower alkoxy or hydroxy substituted analogues, an aralkyl, heterocyclylalkyl or aryl radical, such as benzyl, phenylethyl, phenyl or furfuryl, these radicals being optionally substituted with halogen, nitro, lower alkyl, hydroxy or alkoxy radicals;

$R_1$ can also be a heterocyclic radical having 5 or 6 ring atoms and containing oxygen, sulphur or nitrogen atoms, such as 2- or 3-pyrrolyl, 2- or 3-furyl, 2- or 3-thienyl, 2-, 3- or 4-pyridyl, 2-, 4- or 5- pyrimidinyl, 2- or 3- pyrazolyl, imidazolyl e.g. 1-methyl-2-imidazolyl, triazolyl e.g. 5-methyl-1,2,4-triazol-3-yl, tetrazolyl e.g. 1-methyl-1H-tetrazol-5yl, thiazolyl, thiadiazolyl e.g. 5-methyl-1,3,4-thiadiazol-2yl.

In formula I the dotted line between C-24 and C-25 indicates that the carbon atoms in question are connected with either a double bond or a single bond.

Where not otherwise stated the term lower alkyl in the radicals mentioned above stands for a $C_1$ to $C_4$ alkyl radical.

Of particular interest are compounds in which $Q_1$ and $Q_2$ are both a

group, or one of $Q_1$ or $Q_2$ is oxygen, A represents oxygen or sulphur or a sulphinyl radical, and $R_1$ stands for a straight or branched alkyl group with from 1 to 4 carbon atoms, optionally substituted with halogen atoms, hydroxy groups, or an azido group, and the bond between C-24 and C-25 is either a double bond or a single bond.

Of special quality amongst the just mentioned groups of compounds are those in which $R_1$ is ethyl or isopropyl, optionally substituted with fluorine.

The compounds of the invention can be used as such or in the form of salts or easily hydrolysable esters. The salts of the compounds are especially the pharmaceutically acceptable, non-toxic salts, such as alkali metal salts and alkaline earth metal salts, for example sodium, potassium, magnesium or calcium salts, as well as salts with ammonia or suitable non-toxic amines, such as lower alkyl amines, for example triethylamine, hydroxy-lower alkylamines, for example 2-hydroxyethylamine, bis-(2-hydroxyethyl)-amine or tri-(2-hydroxyethyl)-amine, cycloalkylamines, for example dicyclohexylamine, or benzylamines, for example N,N'-dibenzylethylenediamine, and dibenzylamine.

For certain purposes also the silver salts of the compounds may be used, especially for local treatment.

The easily hydrolysable esters can e.g. by alkanoyloxyalkyl, aralkanoyloxyalkyl, aroyloxyalkyl esters, such as acetoxymethyl, pivaloyloxymethyl, benzoyloxymethyl esters, and the corresponding 1'-oxyethyl derivatives, or alkoxycarbonyloxyalkyl esters, such as methoxycarbonyloxymethyl, ethoxycarbonyloxymethyl esters, and the corresponding 1'-oxyethyl derivatives, or lactonyl esters, such as phthalidyl esters, or dialkylaminoalkyl esters, such as diethylaminoethyl esters.

The antibacterial properties of fusidic acid are well known, and also that variations in the structure may cause a complete loss of such activity.

Now, however, it has been found, that the compounds of the present invention both in vitro and in vivo show interesting antimicrobial and pharmacokinetic properties. Thereby the compounds of the invention can be used in the treatment of bacterial infections in humans and animals. In vitro investigations have for instance shown that the compounds are highly potent against a number of bacteria, e.g. *staphylococci, streptococci, corynebacteriae, neisseriae, clostridiae* and *bacteroides species,* and *Bacillus subtilis;* as can be seen from the following table:

Antibacterial activity of compounds of formula I

| Example | Substituents $Q_1$ | $Q_2$ | A | R | C-24,25 bond | Staph.aureus Leo CC 178B | Strep. pyogenes Leo EC | Strep. species Leo EG2 | Bacillus subtilis Leo KA3 | Bacteroides fragilis Leo JA2 |
|---|---|---|---|---|---|---|---|---|---|---|
| 1 | H,α-OH | H,α-OH | S | $CH(CH_3)_2$ | double | 0.032 | 0.20 | 1.0 | 0.02 | 5.0 |
| 11 | H,α-OH | H,α-OH | S | $CH(CH_3)_2$ | single | 0.016 | 0.04 | 0.10 | 0.008 | 4.0 |
| 35 | H,α-OH | H,α-OH | SO | $CH(CH_3)_2$ | double | 0.050 | 0.20 | 0.32 | 0.40 | 1.3 |
| 42 | H,α-OH | H,α-OH | SO | $CH(CH_3)_2$ | single | 0.040 | 0.16 | 0.50 | 0.16 | 1.6 |
| 32 | H,α-OH | O | S | $CH(CH_3)_2$ | double | 0.020 | 0.20 | 0.63 | 0.02 | 3.2 |
| 33 | H,α-OH | O | S | $CH(CH_3)_2$ | single | 0.040 | 0.32 | 0.79 | 0.05 | 2.0 |
| 34 | O | H,α-OH | S | $CH(CH_3)_2$ | double | 0.040 | 0.40 | 1.0 | 0.05 | 5.0 |
| 46 | H,α-OH | H,α-OH | O | $CH_2CH_3$ | double | 0.025 | 1.0 | 5.0 | 0.05 | 1.0 |
| 75 | H,α-OH | O | O | $CH_2CH_3$ | double | 0.020 | 1.0 | 3.2 | 0.05 | 13 |
| 50 | H,α-OH | H,α-OH | O | $CH_2CH_2F$ | double | 0.020 | 0.63 | 2.5 | 0.05 | 0.32 |
| 76 | H,α-OH | O | O | $CH_2CH_2F$ | double | 0.025 | 1.6 | 4.0 | 0.032 | 2.0 |
| 48 | H,α-OH | H,α-OH | O | $CH_2CF_3$ | double | 0.016 | 0.50 | 1.0 | 0.02 | 32 |
| 52 | H,α-OH | H,α-OH | O | $CH(CH_2F)_2$ | double | 0.025 | 0.50 | 3.2 | 0.04 | 0.63 |
| Fusidic acid | | | | | | 0.032 | 0.79 | 1.6 | 0.20 | 1.6 |

Furthermore the compounds of the invention are chemically more stable than fusidic acid, for instance will the 16-acetoxy group in fusidic acid under certain conditions be hydrolysed to a hydroxy group in which case a considerable decrease of activity takes place. In the compounds of the invention the 16-radicals are not inclined to such hydrolysis, e.g. when 2% (w/v) solutions of the compounds of the invention in aqueous buffer of pH 9.6 were kept at 40° C for 30 days, not even traces of degradation products could be detected by thin layer chromatography. Like fusidic acid the new compounds are absorbed efficiently from the gastro-intestinal tract and are practically non-toxic.

The compounds of formula I can be prepared by a method comprising a first step in which a compound of the general formula II is reacted with a compound of the general formula III to form a compound of the general formula IV

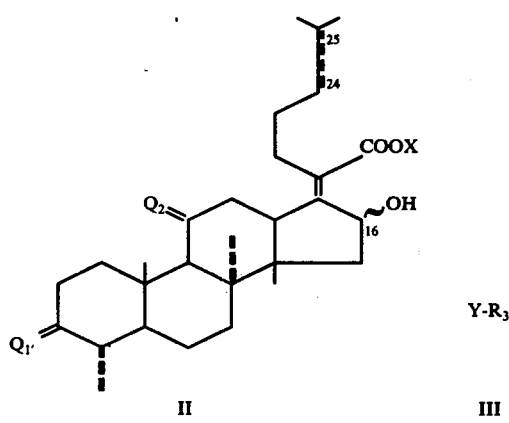

II

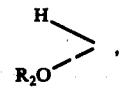

III

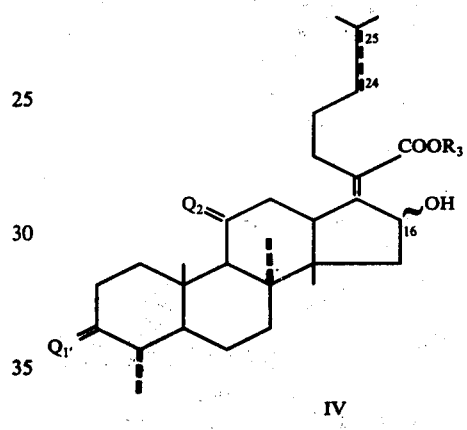

IV in which formulae $Q_1'$ stands for $Q_1$ as defined above or for $R_2$ representing an alkanoyl, an aralkanoyl or an aroyl radical; $Q_2$ and the dotted line between C-24 and C-25 have the meaning as defined above, the wavy line between C-16 and the hydroxyl group indicates that the latter can be α-oriented or β-oriented; X stands for hydrogen or a cation, such as Na+, K+, Ag+, an ammonium or trialkylammonium ion, Y is a chlorine, bromine or iodine atom, and $R_3$ represents a straight or branched alkyl radical having from 1 to 6 carbon atoms, e.g. methyl, ethyl, tert, butyl, an unsubstituted or substituted aralkyl radical, e.g. benzyl, p-nitrobenzyl, or p-methoxybenzyl, an alkanoylmethyl or aroylmethyl radical, e.g. acetonyl or phenacyl, an alkanoyloxyalkyl or aroyloxyalkyl radical, e.g. acetoxymethyl, pivaloyloxymethyl or benzoyloxymethyl, an alkyloxymethyl radical or a cyanomethyl radical.

The reaction is performed in an inert organic solvent, e.g. dimethylformamide, and at room temperature or at slightly elevated temperature.

The preparation of starting compounds of formula II is either known from the literature, is described in our co-pending British complete specification No. 39891/74, or can be performed by analogous methods.

In a second step the compounds of formula IV are converted into compounds of the general formulae Va or Vb:

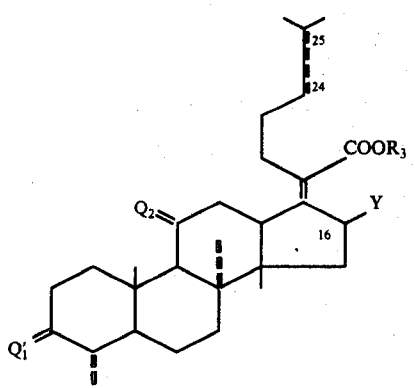
Va

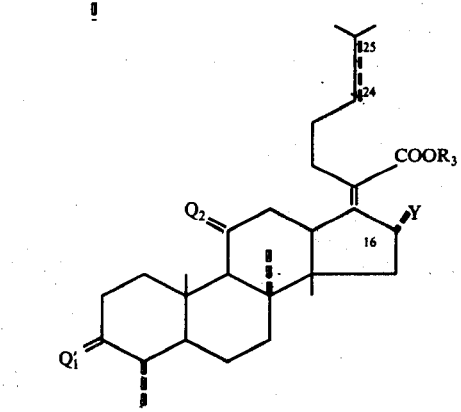
Vb in which formulae $Q_1'$, $Q_2$, $R_3$, Y, and the dotted line between C-24 and C-25 have the meanings as defined above.

The conversion is performed by reacting a compound of formula IV with a polyhalogenomethane, such as tetrachloromethane or tetrabromomethane, or a N-halogenoamide, such as N-chlorosuccinimide, in the presence of triphenylphosphine, a trialkylphosphine, a triaryl phosphite or hexamethylphosphoric triamide, or with an immonium salt of the general formula VI:

$(CH_3)_2N^+=CH-O-R_4 \; Y^-$  VI in which formula $R_4$ represents an unsubstituted or substituted phenyl radical, a phenyloxycarbonyl, alkyl, benzoyl or acetyl radical, and $Y^-$ is a chlorine, bromine or iodine ion. The reaction is performed in an inert organic solvent, e.g. ether, tetrahydrofuran, dimethylformamide, acetonitrile, and at or below room temperature. The compounds of formulae Va and Vb can also be prepared by reacting a compound of formula IV with a phosphorous halide, e.g. phosphorous pentabromide or phosphorous trichloride, with thionyl chloride, or with a (halogenomethylene)-dimethyliminium halide.

The conversion of compounds of the general formula IV into the compounds of the formulae Va and Vb normally produces inversion of configuration at the carbon atom where the substitution takes place (C-16). Thus, a compound of formula IV with an α-oriented hydroxyl group at C-16 is converted into a compound of formula Va, and a compound of formula IV, in which the hydroxyl group at C-16 has β-orientation, is converted into a compound of formula Vb. However, the compounds of formula Va can be transformed into the more stable compounds of formula Vb by reaction with an inorganic or organic halide, e.g. lithium bromide, tetrabutylammonium bromide, sodium bromide, potassium iodide or sodium iodide, in an appropriate organic solvent, preferably dimethylformamide, acetonitrile or acetone, at room temperature or at slightly elevated temperature. When a compound of formula IV in which the hydroxyl group at C-16 is α-oriented is reacted in dimethylformamide with an excess of a compound of formula VI, e.g. phenyl N,N-dimethylformimidate bromide, the originally formed compound of formula Va is converted into a compound of formula Vb during the reaction.

The intermediates for formula Va and Vb are new and interesting compounds which also form a part of this invention.

In a next step the compounds of formula Vb are reacted with compounds of the general formula VII to form, with inversion of configuration at C-16, compounds of the general formula VIII:

$R_1-A-H$  VII

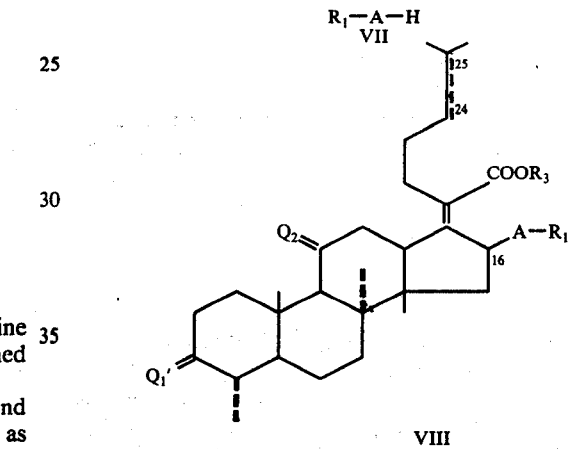
VIII in which formulae $Q_1'$, $Q_2$, $R_1$, $R_3$, and the dotted line between C-24 and C-25 have the meaning as defined above, and A stands for oxygen or sulphur. If A in formulae VII and VIII represents oxygen, the reacting compounds of formula VII may preferably be used as solvents, and the reaction is performed in the presence of a silver or mercury salt, e.g. silver carbonate, silver trifluoroacetate or mercuric acetate, or a base, e.g. potassium carbonate, sodium bicarbonate or sodium alcoholate, and at room temperature or at slightly elevated temperature. If A in formulae VII and VIII stands for sulphur, the reaction is performed in an inert organic solvent, preferably ethanol or dimethylformamide, in the presence of a base, e.g. potassium hydroxide or sodium hydride, and at or below room temperature or at slightly elevated temperature.

In a final step the compounds of formula VIII can be converted into the compounds of formula I by hydrolysis, e.g. in aqueous methanol or ethanol and in the presence of a base, such as sodium or potassium hydroxide or carbonate.

Compounds of formula VIII in which $Q_1'$ and $Q_2$ stand for the group

or O and R₃ represents an easily hydrolyzable ester radical are without further conversion compounds of the invention.

The compounds of formula VIII in which Q₁′ and Q₂ stand for the group

or oxygen, and R₃ represents an unsubstituted or substituted benzyl radical, a cyanomethyl, alkanoylmethyl or aroylmethyl radical can also be converted into compounds of formula I by reduction. In the case that R₃ stands for a benzyl or a cyanomethyl radical, catalytic hydrogenation is preferred, whereas, if R₃ stands for an acetonyl or phenacyl radical, a reduction with zinc in acetic acid can be used.

The compounds of formula I in which Q₁ represents oxygen, and Q₂ stands for oxygen or the group

can also be prepared from the corresponding compounds of formula I in which Q₁, and Q₂ stand for the group

by oxidation methods known to a man skilled in the art.

Compounds of the general formulae I or VIII, in which A stands for a sulfinyl radical are prepared by reacting the corresponding compounds of formulae I or VIII, in which A stands for sulphur, with an oxidizing agent, e.g. hydrogen peroxide, sodium metaperiodate or chromic acid. The reaction is performed in an inert solvent, e.g. water, acetic acid, ethanol or acetone, at or below room temperature or at slightly elevated temperature.

The easily hydrolysable esters of the compounds of formula I can be prepared in known manner by methods described in the literature.

Compounds of the invention in which there are single bonds between C-24 and C-25 can also be prepared from the corresponding unsaturated analogues by reduction, e.g. a catalytic hydrogenation using for instance palladium on carbon as a catalyst.

Intermediates of formula VIII can also be prepared according to one or more of the following methods:

The compounds of the general formula VIII, in which A stands for sulphur and R₁ is aroyl or aromatic heterocyclyl, can be prepared by reacting a compound of the general formula IV, in which the hydroxyl group at C-16 is α-oriented, with a phosphine, e.g. tributylphosphine or triphenylphosphine, and a compound of the general formula R₁SSR₁.

The reaction is performed in an inert organic solvent, preferably dimethylformamide or pyridine, and at or below room temperature.

b. In another embodiment of the method a compound of formula IV, in which the hydroxyl group at C-16 is α-oriented and Q₁′ is different from the group

is reacted with a reactive derivative of an alkylsulphonic or arylsulphonic acid, e.g. an acid chloride or acid anhydride, to form a compound of the general formula IX:

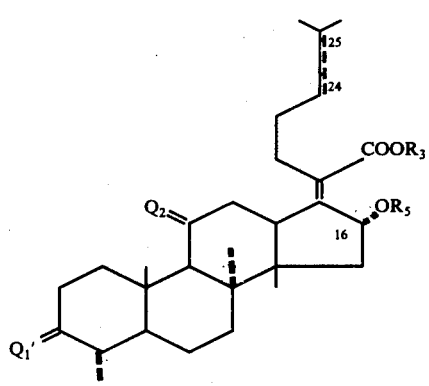

IX in which Q₂, R₃ and the dotted line between C-24 and C-25 are as defined above for compounds of formula IV, Q₁′ stands for oxygen or the group

R₂ being an alkanoyl, aralkanoyl or aroyl radical, and R₅ represents an alkylsulphonyl or arylsulphonyl radical, in particular a methanesulphonyl or a p-toluenesulphonyl group.

In a next step a compound of formula IX is reacted with a compound of the general formula VII to form a compound of the general formula VIII. If A in formulae VII and VIII stands for oxygen, the compounds of formula VII can be used as solvents, and the reaction can be performed at room temperature or at slightly elevated temperature, in some cases in the presence of an organic base, e.g. triethylamine. If A in formulae VII and VIII represents sulphur, the reaction can be performed in the same way as described above for the conversion of compounds of formula Vb into compounds of formula VIII, in which A stands for sulphur.

c. In a further embodiment compounds of the general formula VIII, in which A stands for oxygen, sulphur or a sulfinyl radical, and R₁ represents a hydroxy-substituted alkyl radical, can be converted into corresponding compounds in which R₁ stands for a halogen-substituted alkyl radical by methods described above for the conversion of compounds of formula IV into compounds of formulae Va or Vb.

In the following step, the halogen-substituted alkyl derivatives of formula VIII can be reacted with an aliphatic or aromatic alcohol, preferably in the presence of a silver salt or a base, with an aliphatic or aromatic mercaptan, preferably in the presence of a base, with ammonia or an aliphatic or aromatic amine, or with salts of lower alkanoic acids or benzoic acid, with silver or sodium fluoride, alkalimetal azides, nitrites, cyanides or thiocyanates, or with salts of lower thioalkanoic acids or thiobenzoic acid, to form compounds of formula VIII in which $R_1$ stands for an alkyl radical substituted by e.g. a fluorine atom, an alkyloxy, aralkyloxy, aryloxy, alkylthio, aralkylthio, arylthio, amino, alkylamino, dialkylamino, azido, nitro, cyano, thiocyano, alkanoyloxy, aralkanoyloxy, aroyloxy, alkanoylthio or aroylthio radical.

d. The C-24,25 unsaturated compounds may in some cases advantageously be hydrogenated to the corresponding saturated intermediates of formula VIII.

The compounds of formula VIII can be converted into the compounds of the invention as already described above.

It is a further object of the present invention to provide pharmaceutical compositions which are useful in the treatment of infectious diseases in the human and veterinary practice.

With this object in view, the compositions of the invention contain as an active component at least one member selected from the group consisting of compounds of the formula I, salts thereof with non-toxic, pharmaceutically acceptable bases, and easily hydrolyzable esters together with solid or liquid pharmaceutical carriers and/or diluents.

In the said compositions, the proportion of therapeutically active material to carrier substance can vary between 1% and 95% by weight. The compositions can be worked up to various pharmaceutical forms of presentation, such as granulate, tablets, pills, dragees, suppositories, capsules, sustained-release tablets, suspensions, injection medicine, or so far as mixtures are concerned, they may be filled in bottles or tubes or similar containers. Pharmaceutical organic or inorganic, solid or liquid carriers and/or diluents suitable for oral, enteral, parenteral or topical administration can be used to make up compositions containing the present compounds. Water, gelatine, lactose, starch, magnesium stearate, talc, vegetable and animal oils and fats, benzyl alcohol, gum, polyalkylene gylcol, petroleum jelly, cocoa butter, lanolin or other known carriers for medicaments are all suitable, while stabilizing agents, wetting and emulsifying agents, salts for varying the osmotic pressure or buffers for securing an adequate pH-value of the composition can be used as auxiliary agents.

Furthermore, the composition may contain other pharmaceutically active components which can appropriately be administered together with the compounds of the invention in the treatment of infectious diseases, such as other suitable antibiotics, in particular such antibiotics, which may enhance the activity and/or prevent development of resistance. Such antibiotic include penicillins, cephalosporins, tetracyclines, rifamycins, erythromycin, lincomycin and clindamycin. Other compounds which advantageously may be combined with the compounds of the invention, especially in topical preparations, include e.g. corticosteroids, like hydrocortisone, triamcinolone or fluocinolone.

For granulates, tablets, capsules or dragees the pharmaceutical composition of the invention appropriately contains from 25 percent to 98 percent of the active substance of the invention, and in oral suspensions the corresponding amount is appropriately from 2-25 percent.

For parenteral use the compounds are preferably given by intravenous infusion of an aqueous solution containing from 0.1 to 2 percent of the active ingredient, or the compound might be given by injection of the compounds in pharmaceutical compositions with from 1 to 20 percent active ingredient.

When the compounds are administered in the form of salts with pharmaceutically acceptable non-toxic bases, the preferred salts are for instance the easily water-soluble sodium salts or the diethanolamine salts, but other pharmaceutically acceptable and non-toxic salts may be used, for instance salts which are slightly soluble in water, in order to obtain a particular and appropriate rate of absorption.

As indicated above, the compounds of formula I and their salts may be worked up to pharmaceutical forms of presentation including suspensions, ointments and creams. A pharmaceutical preparation for oral treatment may also be in the form of a suspension of a compound of formula I as such or in the form of a sparingly soluble salt with a pharmaceutically acceptable base, the preparation containing from 20 to 100 mg per ml of vehicle. A pharmaceutical preparation for topical treatment may be in the form of an ointment or cream containing a compound of formula I in an amount of from 0.5 to 10 g per 100 g of preparation.

Another object of the invention resides in the selection of a dose of the compounds of the invention which dose can be administered so that the desired activity is achieved without simultaneous secondary effects. In the human systemic therapy, the compounds and their salts are conveniently administered (to adults) in dosage units containing not less than 50 mg and up to 1000 mg, preferably from 200 to 750 mg, calculated as the compound of formula I.

By the term "dosage unit" is meant a unitary, i.e. a single dose which is capable of being administered to a patient, and which may be readily handled and packed, remaining as a physically stable unit dose comprising either the active material as such or a mixture of it with solid or liquid pharmaceutical diluents or carriers.

In the form of a dosage unit, the compound may be administered once or more times a day at appropriate intervals, always depending, however, on the condition of the patient, and in accordance with the prescription made by the medical practitioner.

Thus in systemic treatment a daily dose will preferably be an amount of from 0.5 to 3 g of a compound of formula I.

By the term "dosage unit" is in connection with the topical use meant a unitary, i.e. a single dose capable of being administered topically to the patients and applicating per sq. centimeter of the infected area from 0.1 mg to 10 mg and preferably from 0.2 mg to 1 mg of the compound in question.

If the composition is to be injected, a sealed ampoule, a vial or a similar container may be provided containing a parenterally acceptable aqueous or oily injectable solution or dispersion of the active material as the dosage unit.

The parenteral preparations are in particular useful in the treatment of conditions in which a quick response to the treatment is desirable. In the continuous therapy of patients suffering from infectious diseases, the tablets or capsules may be the appropriate form of pharmaceutical preparation owing to the prolonged effect obtained when the drug is given orally, in particular in the form of sustained-release tablets.

In the treatment of infectious diseases, such tablets may advantageously contain other active components, as mentioned hereinbefore.

Still another object of the invention is to provide a method of treating patients suffering from infectious diseases, the method comprising administering to adult patients from 0.25 g to 4 g per day, preferably from 0.5 to 3 g per day, of a compound of the formula I or an equivalent amount of a salt as defined before of a compound of the formula I. Preferably, the compound is given in the form of the dosage units aforesaid.

In the following are given some examples on the preparation of intermediates which are illustrative but not limiting for the invention.

Preparation 1

3-O-Acetyl-16-deacetoxy-16α-bromofusidic acid phenacyl ester

A. 3-O-Acetyl-16-epideacetylfusidic acid phenacyl ester

The sodium salt of 3-O-acetyl-16-epideacetylfusidic acid (5.38 g; 10 mmol) and phenacyl bromide (2.2 g; 11 mmol) were dissolved in dimethylformamide (40 ml). After standing for 16 hours at room temperature, the solution was diluted with 150 ml of ether, washed with water (4 × 50 ml), dried, and evaporated in vacuo to give 6.2 g of 3-O-acetyl-16-epideacetylfusidic acid phenacyl ester as a colourless foam.

B. 3-O-Acetyl-16-deacetoxy-16α-bromofusidic acid phenacyl ester

A suspension of dimethylformamide (1.1 ml; 40 mmol) and phenyl chloroformate (5.04 ml; 40 mmol) in 80 ml of petroleum ether (Bp < 50° C) was stirred vigorously at room temperature. During one hour carbophenoxy N,N-dimethylformimidate chloride was formed as colourless crystals. This initial product lost carbon dioxide on further stirring for 16 hours to give crystalline phenyl N,N-dimethylformimidate chloride. This in turn was converted into N,N-dimethylformamide diphenylacetal by adding a solution of phenol (3.76 g; 40 mmol) and triethylamine (5.56 ml; 40 mmol) in ether (10 ml) to the stirred reaction mixture. After stirring for an additional hour, the triethylammonium chloride, formed as a by-product, was filtered off and washed with 50 ml of petroleum ether. When acetyl bromide (2.0 ml; 27 mmol) was added with stirring to the combined filtrate and washing, phenyl N,N-dimethylformimidate bromide was formed as colourless crystals, which were collected and washed with petroleum ether (20 ml) to remove traces of phenyl acetate.

The immonium bromide thus obtained (6 g; 26 mmol) was very hygroscopic, and was immediately added to a solution of 3-O-acetyl-16-epideacetylfusidic acid phenacyl ester (6.2 g; 9.8 mmol) in dimethylformamide (40 ml). After standing for 48 hours at room temperature, this solution was diluted with ether (100 ml), washed with 0.1 N sodium hydroxide (100 ml) and water (3 × 50 ml), dried, and evaporated in vacuo. Addition of methanol (50 ml) caused by residue to crystallize. The crystals were filtered off, washed with methanol, and dried to afford 5.2 g of 3-O-acetyl-16-deacetoxy-16α-bromofusidic acid phenacyl ester, melting point 141°–142° C.

Preparations 2–8

3-O-Acetyl-16-deacetoxy-16α-bromofusidic acid esters

A. By following the procedure of Preparation 1 A but substituting the esterifying agents shown in table I for the phenacyl bromide, the 3-O-acetyl-16-epideacetylfusidic acid esters indicated in table I were obtained.

B. By substituting the 3-O-acetyl-16-epideacetylfusidic acid esters indicated in table I for the 3-O-acetyl-16-epideacetylfusidic acid phenacyl ester in the procedure of Preparation 1 B, the 3-O-acetyl-16-deacetoxy-16α-bromofusidic acid esters shown in table I were obtained.

Table I

| Preparation | Esterifying agent | Resulting compounds | | |
|---|---|---|---|---|
| | | $R_1$ | $R_2$ | Mp (° C) |
| 2 A | chloromethyl acetate | OH | $CH_2OCOCH_3$ | amorphous |
| 2 B | | Br | $CH_2OCOCH_3$ | 102–105 |
| 3 A | chloromethyl pivalate | OH | $CH_2OCOC(CH_3)_3$ | amorphous |
| 3 B | | Br | $CH_2OCOC(CH_3)_3$ | amorphous |
| 4 A | chloromethyl benzoate | OH | $CH_2OCOC_6H_5$ | amorphous |
| 4 B | | Br | $CH_2OCOC_6H_5$ | 93–94 |
| 5 A | chloroacetonitrile | OH | $CH_2CN$ | amorphous |
| 5 B | | Br | $CH_2CN$ | 122–123 |
| 6 A | benzyl bromide | OH | $CH_2C_6H_5$ | 108–109 |
| 6 B | | Br | $CH_2C_6H_5$ | 128–129 |
| 7 A | p-methyl benzyl bromide | OH | $CH_2C_6H_4CH_3$ | amorphous |
| 7 B | | Br | $CH_2C_6H_4CH_3$ | amorphous |
| 8 A | chloromethyl methyl ether | OH | $CH_2OCH_3$ | amorphous |
| 8 B | | Br | $CH_2OCH_3$ | amorphous |

Preparation 9

3-O-Acetyl-16-deacetoxy-16α-bromofusidic acid p-nitrobenzyl ester

The sodium salt of 3-O-acetyl-16-epideacetylfusidic acid (21.5 g; 40 mmol) and p-nitrobenzyl bromide (9.5 g; 44 mmol) were dissolved in dimethylformamide (200 ml). This solution was left at room temperature for 16 hours, during which period 3-O-acetyl-16-epideacetylfusidic acid p-nitrobenzyl ester was formed. Phenyl N,N-dimethylformimidate bromide (36 g; see Preparation 1 B for the preparation of this reagent) was then added, and the resulting red-brown solution was kept at room temperature for 48 hours. Methanol (700 ml) and water (280 ml) were added with stirring to precipitate a crystalline product. The crystals were filtered off, washed with methanol:water 3:1, and dried to afford 26.1 g of 3-O-acetyl-16-deacetoxy-16α-bromofusidic acid p-nitrobenzyl ester, melting point: 151°–157° C. Recrystallization from methanol:water gave the analytically pure compound, melting point: 157°–159° C.

Preparations 10–12

3-O-Acetyl-16-deacetoxy-16α-bromofusidic acid esters

By following the procedure of Preparation 9 but substituting the esterifying agents listed in table II for p-nitrobenzyl bromide, the 3-O-acetyl-16-deacetoxy-16α-bromofusidic acid esters shown in table II were obtained.

Table II

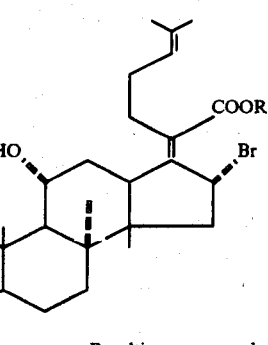

| Preparation | Esterifying agent | Resulting compounds R | Mp (° C) |
|---|---|---|---|
| 10 | p-benzylphenacyl bromide | CH₂COC₆H₄CH₂C₆H₅ | 127–129 |
| 11 | p-methoxyphenacyl bromide | CH₂COC₆H₄OCH₃ | 114–116 |
| 12 | bromoacetone | CH₂COCH₃ | 80–81 |

Preparation 13

3-O-Acetyl-16-deacetoxy-16α-bromofusidic acid benzyl ester

A. 3-O-Acetyl-16-deacetylfusidic acid benzyl ester.

To the sodium salt of 16-deacetylfusidic acid (84.7 g; 0.17 mol) in dimethylformamide (200 ml) was added benzyl bromide (25 ml; 0.21 mol). After stirring for 5 hours at room temperature, the resulting solution was cooled to 0° C, and pyridine (200 ml; 2.5 mol) and acetic anhydride (170 ml; 1.8 mol) were added. After standing for 16 hours at room temperature, the mixture was again cooled to 0° C, and 50 ml of water was added with stirring at such a rate, that the temperature remained below 15° C (about 1 hour was required for this addition). Then methanol (800 ml) and water (400 ml) were added to complete the precipitation of the desired product, which, after stirring for 1 hour at 10° C, was filtered off, washed with ice-cold methanol (3 × 20 ml), and dried to yield 68 g of 3-O-acetyl-16-deacetylfusidic acid benzyl ester as colourless crystals, melting point 154°–158° C.

B. 3-O-Acetyl-16-deacetoxy-16α-bromofusidic acid benzyl ester

The above benzyl ester (68 g; 112 mmol), sodium bromide (46.2 g; 448 mmol) pyridine (22 ml; 276 mmol) and dimethylformamide (400 ml) was stirred for 30 minutes at room temperature and then cooled to 0° C. Phenyl chloroformate (56.5 ml; 448 mmol) was added over a period of 45 minutes, and the resulting mixture was stirred at room temperature for 18 hours. After this period, the reaction product was precipitated by addition of methanol (400 ml) and water (300 ml) as colourless crystals, which were filtered off, washed with methanol:water (2 × 60 ml of a 2:1 mixture) and petroleum ether (3 × 30 ml), and dried to yield 62.9 g of 3-O-acetyl-16-deacetoxy-16α-bromofusidic acid benzyl ester, melting point 124°–126° C.

Preparations 14-15

3-O-Acetyl-16-deacetoxy-16α-bromofusidic acid esters

A. Following the procedure of Preparation 13 A but substituting phenacyl bromide or p-nitrobenzyl bromide for the benzyl bromide, the 3-O-acetyl-16-deacetylfusidic acid esters indicated in table III were obtained.

B. By substituting the 3-O-acetyl-16-deacetylfusidic acid esters shown in table III for the 3-O-acetyl-16-deacetylfusidic acid benzyl ester in the procedure of Preparation 13 B, the 3-O-acetyl-16-deacetoxy-16α-bromofusidic acid esters indicated in table III were obtained.

Table III

| Preparation | R₁ | Resulting compounds R₂ | Mp (° C) |
|---|---|---|---|
| 14 A | β-OH | CH₂COC₆H₅ | 149–151 |
| 14 B | α-Br | CH₂COC₆H₅ | 141–142 |
| 15 A | β-OH | CH₂C₆H₄NO₂ (p) | 141–143 |
| 15 B | α-Br | CH₂C₆H₄NO₂ (p) | 157–159 |

Preparation 16

3-O-Acetyl-16-deacetoxy-16α-bromofusidic acid pivaloyloxymethyl ester

A. 3-O-Acetyl-16-deacetoxy-16β-bromofusidic acid pivaloyloxymethyl ester

3-O-Acetyl-16-epideacetylfusidic acid pivaloyloxymethyl ester (17.4 g; 28 mmol) was dissolved in dry ether (200 ml), and triphenylphosphine (16 g; 60 mmol) and tetrabromomethane (20 g; 60 mmol) was added. After stirring for 16 hours at room temperature, the reaction mixture was filtered to remove triphenylphosphine oxide, which was formed as a by-product. The filtrate was evaporated in vacuo, and the residue was purified by dry column chromatography on silica gel (cyclohexane:ethyl acetate 8:2) to give 10.6 g of 3-O-acetyl-16-deacetoxy-16β-bromofusidic acid pivaloyloxymethyl ester as colourless crystals, obtained from ether-petroleum ether, melting point 120°–122° C. Recrystallization from ether-petroleum ether afforded the analytically pure compound, melting point 120°–122° C.

B. 3-O-Acetyl-16-deacetoxy-16α-bromofusidic acid pivaloyloxymethyl ester

The 3-O-acetyl-16-deacetoxy-16β-bromofusidic acid pivaloyloxymethyl ester described above (5 g) was epimerized to the 16β-compound by reacting with tetrabutylammonium bromide (5 g) in acetonitrile (60 ml) for three days at room temperature. The reaction mixture was evaporated in vacuo, and ether was added to the residue causing tetrabutylammonium bromide to crystallize. The crystals were filtered off, and the filtrate was washed with water (2 × 50 ml), dried, and evaporated in vacuo to yield 4.87 g of 3-O-acetyl-16-deacetoxy-16α-bromofusidic acid pivaloyloxymethyl ester as a colourless gum.

Preparation 17

3-O-Acetyl-16-deacetoxy-16α-bromofusidic acid acetoxymethyl ester

A. 3-O-Acetyl-16-deacetoxy-16β-bromofusidic acid acetoxymethyl ester

By following the procedure described in Preparation 16 A and substituting 3-O-acetyl-16-epideacetylfusidic acid acetoxymethyl ester for the 3-O-acetyl-16-epideacetylfusidic acid pivaloyloxymethyl ester, 3-O-acetyl-16-deacetoxy-16β-bromofusidic acid acetoxymethyl ester was prepared, melting point 119°–120° C.

B. 3-O-Acetyl-16-deacetoxy-16α-bromofusidic acid acetoxymethyl ester

By following the procedure described in Preparation 16 B and substituting 3-O-acetyl-16-deacetoxy-16β-bromofusidic acid acetoxymethyl ester for the 3-O-acetyl-16-deacetoxy-16β-bromofusidic acid pivaloyloxymethyl ester, 3-O-acetyl-16-deacetoxy-16α-bromofusidic acid acetoxymethyl ester, melting point 102°–105° C, was prepared.

Preparation 18

3-O-Acetyl-16-deacetoxy-16α-bromo-24,25-dihydrofusidic acid phenacyl ester

A. 16-Deacetyl-24,25-dihydrofusidic acid phenacyl ester

To a solution of 16-deacetyl-24,25-dihydrofusidic acid sodium salt (4.99 g; 10 mmol) in dimethylformamide (25 ml) was added phenacyl bromide (1.99 g; 10 mmol), and the mixture was stirred at room temperature for 4 hours. After dilution with ether (100 ml), the mixture was washed with water (4 × 25 ml). The organic phase was separated, dried, and concentrated to about 20 ml whereby a crystalline product precipitated. After being kept in the refrigerator for 2 hours, the crystals were filtered off, washed with ether, and dried to afford 4.52 g of the desired compound, melting point 92°–94° C. (dec.).

B. 3-O-Acetyl-16-deacetyl-24,25-dihydrofusidic acid phenacyl ester

To a stirred solution of 16-deacetyl-24,25-dihydrofusidic acid phenacyl ester (2.38 g; 4 mmol) in pyridine (8 ml) was added acetic anhydride (4 ml), and the mixture was left at room temperature for 16 hours. After dilution of the stirred reaction mixture with diisopropyl ether (60 ml), crystallization of a colourless product occurred. The crystals were collected, washed with diisopropyl ether and dried to yield 1.92 g of the desired compound, melting point 133°–135° C.

C. 3-O-Acetyl-16-deacetoxy-16α-bromo-24,25-dihydrofusidic acid phenacyl ester

Phenyl chloroformate (1.26 ml; 10 mmol) was added dropwise at 0° C to a stirred solution of 3-O-acetyl-16-deacetyl-24,25-dihydrofusidic acid phenacyl ester (1.59 g; 2.5 mmol), sodium bromide (1.03 g; 10 mmol), and pyridine (0.52 ml; 6.5 mmol) in dimethylformamide (15 ml). After the addition was finished (~15 min.), the reaction mixture was stirred for 2 hours at 0° C, followed by 16 hours at room temperature. Dropwise addition of methanol:water 1:1 (15 ml) to the stirred mixture precipitated a crystalline product which was filtered off, washed with methanol, and dried to give 1.22 g of the desired compound, melting point 127°–129° C. Recrystallization from methylene chloride-methanol gave the analytical sample, melting point 130°–132° C.

Preparations 19–20

3-O-Acetyl-16-deacetoxy-16α-bromo-24,25-dihydrofusidic acid esters

A. By substituting benzyl bromide or p-nitrobenzyl bromide for the phenacyl bromide in the procedure of Preparation 18 A, the 16-deacetyl-24,25-dihydrofusidic acid esters indicated in table IV below were obtained.

B. Following the procedure of Preparation 18 B, but substituting the 16-deacetyl-24,25-dihydrofusidic acid esters shown in table IV for the 16-deacetyl-24,25-dihydrofusidic acid phenacyl ester, the 3-O-acetyl ester derivatives indicated in table IV were obtained.

C. Following the procedure of Preparation 18 C, but substituting the 3-O-acetyl-16-deacetyl-24,25-dihydrofusidic acid esters shown in table IV for the 3-O-acetyl-16-deacetyl-24,25-dihydrofusidic acid phenacyl ester, the 3-O-acetyl-16-deacetoxy-16α-bromo-24,25-dihydrofusidic acid esters indicated in table IV were obtained.

Table IV

| Preparation | R$_1$ | R$_2$ | R$_3$ | Mp (° C) |
|---|---|---|---|---|
| 19 A | H | β-OH | CH$_2$C$_6$H$_5$ | amorphous |
| 19 B | CH$_3$CO | β-OH | CH$_2$C$_6$H$_5$ | 162–163 |
| 19 C | CH$_3$CO | α-Br | CH$_2$C$_6$H$_5$ | 104–105 |
| 20 A | H | β-OH | CH$_2$C$_6$H$_4$NO$_2$ | amorphous |
| 20 B | CH$_3$CO | β-OH | CH$_2$C$_6$H$_4$NO$_2$ | amorphous |
| 20 C | CH$_3$CO | α-Br | CH$_2$C$_6$H$_4$NO$_2$ | 147–149 |

Resulting compounds

Preparation 21

3-O-Formyl-16-deacetoxy-16α-bromofusidic acid benzoyloxymethyl ester

A. 16-Epideacetylfusidic acid benzoyloxymethyl ester

16-Epideacetylfusidic acid (35.5 g; 75 mmol) was dissolved in methanol (150 ml) and converted into its sodium salt by titration with 5 N sodium hydroxide using phenolphthalein as indicator. After evaporation to dryness in vacuo, the resulting amorphous sodium salt was dissolved in dimethylformamide (150 ml), chloromethyl benzoate (14.08 g; 82.5 mmol) was added, and the mixture was stirred at room temperature for 16 hours. Water (200 ml) was added, and the mixture was extracted with ether (400 ml). The organic phase was separated, washed with water (4 × 100 ml), dried, and evaporated in vacuo to yield 44.6 g of 16-epideacetylfusidic acid benzoyloxymethyl ester as an amorphous product.

B. 3-O-Formyl-16-deacetoxy-16α-bromofusidic acid benzoyloxymethyl ester

The 16-epideacetylfusidic acid benzoyloxymethyl ester prepared above was dissolved in dimethylformamide (300 ml), phenyl N,N-dimethylformimidate bromide (67 g; ca. 290 mmol) was added with stirring, and the red-brown solution was kept at 5° C for 6–7 days. To the mixture was added methanol (150 ml), and, with vigorous stirring, water (150 ml) from a separating funnel to precipitate a crystalline product. The crystals were filtered off, washed with methanol:water 1:1, and dried to afford 27.1 g of 3-O-formyl-16-deacetoxy-16α-bromofusidic acid benzoyloxymethyl ester, melting point 131°–135° C. Two recrystallizations from ether-methanol raised the melting point to 140°–142° C.

Preparations 22-24

3-O-Formyl-16-deacetoxy-16α-bromofusidic acid esters

A. By substituting benzyl bromide, chloromethyl pivalate or chloromethyl acetate for the chloromethyl benzoate in the procedure of Preparation 21 A the 16-epideacetylfusidic acid esters indicated in table V below were obtained.

B. Following the procedure of Preparation 21 B, but substituting the 16-epideacetylfusidic acid esters shown in table V for the 16-epideacetylfusidic acid benzoyloxymethyl ester, the 3-O-formyl-16-deacetoxy-16α-bromofusidic acid esters indicated in table V were obtained.

Table V

Resulting compounds

| Preparation | $R_1$ | $R_2$ | $R_3$ | Mp (° C) |
|---|---|---|---|---|
| 22 A | H | OH | $CH_2C_6H_5$ | 95-98 |
| 22 B | HCO | Br | $CH_2C_6H_5$ | 125-127 |
| 23 A | H | OH | $CH_2OCOC(CH_3)_3$ | amorphous |
| 23 B | HCO | Br | $CH_2OCOC(CH_3)_3$ | amorphous |
| 24 A | H | OH | $CH_2OCOCH_3$ | amorphous |
| 24 B | HCO | Br | $CH_2OCOCH_3$ | 123-125 |

Preparation 25

3-O-Formyl-16-deacetoxy-16α-bromofusidic acid benzyl ester

A. 16-Deacetylfusidic acid benzyl ester

To a solution of 16-deacetylfusidic acid sodium salt (4.97 g; 10 mmol) in dimethylformamide (25 ml) was added benzylbromide (1.5 ml; 12.5 mmol), and the mixture was stirred at room temperature for 4 hours. After addition of water (100 ml), the mixture was extracted with ether (2 × 50 ml), and the combined organic extracts were washed with water (4 × 20 ml), dried, and evaporated in vacuo. The residue thus obtained was dissolved in ether (50 ml), and on addition of petroleum ether (50 ml) with stirring a crystalline product precipitated. The crystals were filtered off, washed with ether:petroleum ether 1:2, and dried to give 4.92 g of the desired compound, melting point 117°–119° C.

B. 3-O-Formyl-16-deacetylfusidic acid benzyl ester

Acetic formic anhydride (4 ml) was added dropwise at 0° C to a stirred solution of 16-deacetylfusidic acid benzyl ester (4.52 g; 8 mmol) in pyridine (8 ml), and the mixture was kept at the low temperature for 15 minutes. On dilution of the stirred reaction mixture with diisopropyl ether (40 ml), a crystalline product precipitated. After being kept in the refrigerator for 2 hours, the crystals were collected, washed with diisopropyl ether, and dried to yield 4.04 g of the desired compound, melting point 143°–145° C. Recrystallization from ether-diisopropyl ether afforded the analytical sample, melting point 145°–147° C.

C. 3-O-Formyl-16-deacetoxy-16α-bromofusidic acid benzyl ester.

By following the procedure of Preparation 13 B and substituting the above 3-O-formyl-16-deacetylfusidic acid benzyl ester for the 3-O-acetyl-16-deacetylfusidic acid benzyl ester, 3-O-formyl-16-deacetoxy-16α-bromofusidic acid benzyl ester was prepared as colourless crystals; melting point 125°–127° C.

Preparation 26

3-O-Formyl-16-deacetoxy-16α-bromofusidic acid pivaloyloxymethyl ester

A. 16-Deacetylfusidic acid pivaloyloxymethyl ester

To a solution of the amorphous silver salt of 16-deacetylfusidic acid (5.8 g; 10 mmol) in dimethylformamide (50 ml) was added chloromethyl pivalate (1.48 ml; 10 mmol), and the mixture was stirred at room temperature for 48 hours. Filter aid was used to remove insoluble material, which was washed with ether (2 × 25 ml). The combined filtrate and washings were diluted with ether (100 ml), the resulting mixture was washed with water (4 × 50 ml), and the organic phase dried and evaporated in vacuo to afford the crude ester as a yellowish foam. Purification of the residue by dry column chromatography on silica gel (developing solvent: Cyclohexane:ethyl acetate 3:7) yielded the desired ester as an amorphous product which failed to crystallize.

The NMR spectrum ($CDCl_3$) shows signals at $\delta$ = 0.90 (d, 3H), 0.93 (s, 3H), 0.98 (s, 3H), 1.22 (s, 9H; $C(C\underline{H}_3)_3$), 1.38 (s, 3H), 1.62 and 1.68 (2 bs, 6H), 2.99 (m, 1H; $C\underline{H}$-13), 3.77 (m, 1H; $C\underline{H}$-3), 4.33 (m, 1H; $C\underline{H}$-11), 5.00 (m, 1H; $C\underline{H}$-16), 5.12 (m, 1H; $C\underline{H}$-24), and 5.15 and 5.42 (2 d, J=7, 2H; $OC\underline{H}_2O$) ppm. Tetramethylsilane was used as internal reference.

B. 3-O-Formyl-16-deacetylfusidic acid pivaloyloxymethyl ester

Following the procedure of Preparation 25 B, but substituting 16-deacetylfusidic acid pivaloyloxymethyl ester for the 16-deacetylfusidic acid benzyl ester, the 3-O-formyl-16-deacetylfusidic acid pivaloyloxymethyl ester was obtained.

C. 3-O-Formyl-16-deacetoxy-16α-bromofusidic acid pivaloyloxymethyl ester

By substituting 3-O-formyl-16-deacetylfusidic acid pivaloyloxymethyl ester for the 3-O-acetyl-16-deacetylfusidic acid benzyl ester in the procedure of Preparation 13 B, 3-O-formyl-16-deacetoxy-16α-bromofusidic acid pivaloyloxymethyl ester was obtained as a colourless foam.

The NMR spectrum (CDCl$_3$) shows signals at δ = 0.78 (s, 3H), 0.87 (d, J=7, 3H), 1.00 (s, 3H); 1.23 (s, 9H, C(C$\underline{H}_3$)$_3$), 1.47 (s, 3H), 1.61 and 1.68 (2 bs, 6H), 3.45 (m, 1H; C$\underline{H}$-13), 4.35 (m, 1H; C$\underline{H}$-11), 5.08 (m, 1H; C$\underline{H}$-3), 5.12 (m, 1H, C$\underline{H}$-24), 5.62 (bt, 1H, C$\underline{H}$-16), 5.82 and 5.92 (2 d, J=6, 2H; OC$\underline{H}_2$O), and 8.15 (bs, 1H, $\underline{H}$CO) ppm. Tetramethylsilane was used as internal reference.

Preparation 27

3-O-Formyl-16-deacetoxy-16α-bromo-24,25-dihydrofusidic acid acetoxymethyl ester

A. 16-Epideacetyl-24,25-dihydrofusidic acid acetoxymethyl ester

To a solution of 16-epideacetyl-24,25-dihydrofusidic acid potassium salt (20.6 g; 40 mmol) in dimethylformamide (160 ml) was added chloromethyl acetate (4.0 ml; 44 mmol), and the mixture was stirred at room temperature for 18 hours. After dilution with ether (500 ml), the mixture was washed with water (2 × 150 ml, 4 × 75 ml), and the organic layer was dried and evaporated in vacuo to give the desired compound as a colourless foam.

B. 3-O-Formyl-16-deacetoxy-16α-bromo-24,25-dihydrofusidic acid acetoxymethyl ester To a stirred solution of the above ester (40 mmol) and sodium bromide (20.6 g; 0.2 mol) in dimethylformamide (200 ml) was added dropwise at 0° C phenyl chloroformate (25.2 ml; 0.2 mol). After the addition was finished (about 45 minutes), the mixture was stirred at 0° C for 3–4 hours and at room temperature for a further 10–12 hours. Precipitated sodium chloride was filtered off and washed with dimethylformamide (2 × 25 ml). To the combined filtrate and washings was added methanol:water 1:1 (300 ml) with stirring to precipitate a crystalline product. The crystals were filtered off, washed with methanol:water 1:1, dried, and finally recrystallized from ether-diisopropyl ether to afford 15.35 g of the desired compound, melting point 126°–127° C.

Preparations 28–32

16-Deacetoxy-16α-bromofusidic acid esters

By substituting 16-epideacetylfusidic acid benzyl, phenacyl, pivaloyloxymethyl, acetoxymethyl or benzoyloxymethyl ester for the 3-O-acetyl-16-epideacetylfusidic acid pivaloyloxymethyl ester in the procedure of Preparation 16, the 16-deacetoxy-16α-bromofusidic acid esters listed in table VI were obtained.

Table VI

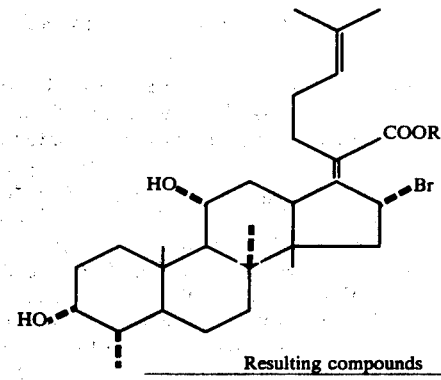

| Preparation | R | Mp (° C) |
|---|---|---|
| 28 | CH$_2$C$_6$H$_5$ | amorphous |
| 29 | CH$_2$COC$_6$H$_5$ | amorphous |
| 30 | CH$_2$OCOC(CH$_3$)$_3$ | amorphous |
| 31 | CH$_2$OCOCH$_3$ | 105–106 |
| 32 | CH$_2$OCOC$_6$H$_5$ | amorphous |

Preparation 33

3-O-Acetyl-11-keto-16α-bromofusidic acid phenacyl ester

To a solution of 3-O-acetyl-16-deacetoxy-16α-bromofusidic acid phenacyl ester (6.98 g; 10 mmol) in acetone (70 ml) was added Jones reagent (3.0 ml), and the mixture was stirred for 30 minutes at room temperature. After dilution with ether (100 ml) and addition of water (70 ml), the mixture was stirred for a further 10 minutes. The organic layer was separated and the aqueous layer reextracted with ether (100 ml). The combined organic extracts were washed with water until neutral, dried, and concentrated to about 50 ml, whereby precipitation of a colourless crystalline product occurred. After being kept in the refrigerator for 1 hour, the crystals were filtered off, washed with ice-cold ether, and dried to give 5.37 g of 3-O-acetyl-11-keto-16-deacetoxy-16α-bromofusidic acid phenacyl ester, melting point 120°–121° C. On concentration of the mother liquor another 0.95 g of the desired compound, melting point 114°–116° C, was obtained. Recrystallization from methylene chloride - diisopropyl ether afforded the analytical sample, melting point 120°–121° C.

Preparation 34

3-O-Acetyl-11-keto-16-deacetoxy-16α-bromofusidic acid benzyl ester

By following the procedure of Preparation 33 and substituting 3-O-acetyl-16-deacetoxy-16α-bromofusidic acid benzyl ester for 3-O-acetyl-16-deacetoxy-16α-bromofusidic acid phenancyl ester, 3-O-acetyl-11-keto-16-deacetoxy-16α-bromofusidic acid benzyl ester was prepared as a colourless foam.

The NMR spectrum (CDCl$_3$) shows signals at δ = 1.00 (s, 3H), 1.05 (s, 3H), 1.02 (d, 3H), 1.27 (s, 3H), 1.62 and 1.68 (2 bs, 6H), 2.06 (s, 3H; C$\underline{H}_3$CO), 3.30 (m, 1H; C$\underline{H}$-13), 4.95 (m, 1H, C$\underline{H}$-3), 5.05 (m, 1H, C$\underline{H}$-24), 5.22 (s, 2H; C$\underline{H}_2$C$_6$H$_5$), 5.60 (bt, 1H; C$\underline{H}$-16), and 7.35 (s, 5H; arom. C$\underline{H}$) ppm. Tetramethylsilane was used as internal reference.

Preparation 35

3-O-Formyl-11-keto-16α-bromo-24,25-dihydrofusidic acid acetoxymethyl ester

By substituting 3-O-formyl-16-deacetoxy-16α-bromo-24,25-dihydrofusidic acid acetoxymethyl ester for the 3-O-acetyl-16α-bromofusidic acid phenacyl ester in the procedure of Preparation 33 3-O-formyl-11-keto-16-deacetoxy-16α-bromo-24,25-dihydrofusidic acid acetoxymethyl ester was obtained as a colourless foam. The NMR spectrum (CDCl$_3$) shows signals at $\delta$ = 0.87 (d, J=5.5, 6H), 1.02 (s, 3H), 1.04 s, 3H), 1.25 (s, 3H), 2.12 (s, 3H; C$\underline{H}_3$CO), 3.35 (m, 1H; C$\underline{H}$-13), 5.10 (m, 1H; C$\underline{H}$-3), 5.68 (bt, 1H; C$\underline{H}$-16), 5.81 and 5.90 (2 d, J=5.5, 2H; OC$\underline{H}_2$O), and 8.15 (bs, 1H; $\underline{H}$CO) ppm. Tetramethylsilane was used as internal reference.

Preparation 36

3-Keto-16-deacetoxy-16α-bromofusidic acid acetoxymethyl ester

A. 3-Keto-16-epideacetylfusidic acid acetoxymethyl ester

To a solution of 3-keto-16-epideacetylfusidic acid potassium salt (3.06 g; 6 mmol) in dimethylformamide (30 ml) was added chloromethyl acetate (0.6 ml; 6.6 mmol), and the mixture was stirred at room temperature for 18 hours. The reaction mixture was diluted with ether (100 ml) and washed with water (4 × 30 ml). The organic phase was separated, dried, and evaporated in vacuo to afford 3.2 g of the desired compound as a colourless foam.

B. 3-Keto-16-deacetoxy-16α-bromofusidic acid acetoxymethyl ester

By following the procedure described in Preparation 27 B but substituting the above 3-keto-16-epideacetylfusidic acid acetoxymethyl ester for the 16-epideacetyl-24,25-dihydrofusidic acid acetoxymethyl ester, 3-keto-16-deacetoxy-16α-bromofusidic acid acetoxymethyl ester, melting point 144°–145° C, was obtained.

Preparation 37

3-O-Acetyl-16-deacetoxy-16α-chlorofusidic acid methoxymethyl ester

3-O-Acetyl-16-epideacetylfusidic acid methoxymethyl ester (1.4 g; 2.5 mmol), triphenylphosphine (2.6 g; 10 mmol) and N-chlorosuccinimide (1.3 g; 10 mmol) were dissolved in dry ether (50 ml). After standing for one hour at 35° C, the triphenylphosphine oxide which precipitated was filtered off, and the filtrate was evaporated in vacuo. The residue was purified by dry column chromatography on silica gel (cyclohexane:ethyl acetate 7:3) to afford 1.14 g of 3-O-acetyl-16-deacetoxy-16β-chlorofusidic acid methoxymethyl ester, which was crystallized from petroleum ether, melting point 140°–151° C. Recrystallization from cyclohexane afforded the analytically pure compound, melting point 149°–151° C.

Preparation 38

3-O-Acetyl-16-deacetoxy-16β-chlorofusidic acid benzyl ester

Carbophenoxy N,N-dimethylformimidate chloride was prepared by adding phenyl chloroformate (0.3 ml; 2.4 mmol) to N,N-dimethylformamide (15 ml). To the resulting solution was added 3-O-acetyl-16-epideacetylfusidic acid benzyl ester (500 mg; 0.82 mmol). After standing for 16 hours at room temperature the reaction mixture was diluted with ether (100 ml), washed with 2 N sodium hydroxide (25 ml) and water (3 × 25 ml), dried and evaporated in vacuo to give 480 mg of 3-O-acetyl-16-deacetoxy-16β-chlorofusidic acid benzyl ester, which was crystallized from ether-petroleum ether, melting point 163°–165° C. Recrystallization from ethyl acetate-petroleum ether afforded the analytically pure command, melting point 165°–166° C.

Preparation 39

3-O-Acetyl-16-deacetoxy-16α-chlorofusidic acid benzyl ester

To a stirred ice-cooled solution of 3-O-acetyl-16-deacetylfusidic acid benzyl ester (1.36 g) in dimethylformamide (10 ml) and pyridine (0.44 ml) was added phenyl chloroformate (1.13 ml) over a period of 30 minutes. After stirring at room temperature for 16 hours, the resulting solution was diluted with ether (100 ml), washed with 2 N sodium hydroxide (25 ml) and water (3 × 50 ml), dried and evaporated in vacuo. The residue was dissolved in ether (10 ml) and petroleum ether was added to precipitate the reaction product as colourless crystals, which were filtered off, washed with petroleum ether, and dried to yield 3-O-acetyl-16-deacetoxy-16α-chlorofusidic acid benzyl ester, melting point 115°–117° C. Recrystallization from ethyl acetate-petroleum ether raised the melting point to 120°–122° C.

The invention will be further described in the following Examples which are not to be construed as limiting the invention.

EXAMPLE 1

16-Deacetoxy-16β-isopropylthiofusidic acid

A. 3-O-Acetyl-16-deactoxy-16β-isopropylthiofusidic acid p-nitrobenzyl ester

3-O-Acetyl-16-deacetoxy-16α-bromofusidic acid p-nitrobenzyl ester (28.6 g; 40 mmol) was added to a solution of potassium hydroxide (10 g of 85% purity; 150 mmol) and isopropyl mercaptan (30 ml; 320 mmol) in ethanol (1000 ml), and the suspension was stirred for four days. Thereafter, 500 ml of water was added to complete the precipitation of the desired product. The crystals were filtered off, washed with water:ethanol (1:2), and dried to give 21.5 g of crude 3-O-acetyl-16-deacetoxy-16β-isopropylthiofusidic acid p-nitrobenzyl ester, melting point: 157°–161° C.

B. 16-Deacetoxy-16β-isopropylthiofusidic acid

A suspension of the above p-nitrobenzyl ester in a mixture of ethanol (800 ml) and 2 N aqueous sodium hydroxide (200 ml) was heated to 60° C for 3 hours. The resulting dark solution was acidified with 4 N hydrochloric acid (125 ml) and treated for 15 minutes with 5 g of charcoal while still hot. After filtration, 500 ml of water was added, and, after cooling to room temperature, the crystalline product was filtered off, washed with water, and dried to give 14.1 g of 16-deacetoxy-16β-isopropylthiofusidic acid, melting point: 223°–229° C. Recrystallization from 2-butanone gave the analytically pure compound, melting point: 229°–231° C.

EXAMPLES 2-8

16β-Thioethers of 16-deacetoxyfusidic acid

A. 16β-Thioethers of 3-O-acetyl-16-deacetoxyfusidic acid p-nitrobenzyl ester By following the procedure described in Example 1 A and substituting the mercaptans listed in table VII for isopropyl mercaptan, the 16β-thioethers of 3-O-acetyl-16-deacetoxyfusidic acid p-nitrobenzyl ester indicated in table VII were prepared.

Table VII

| | | Resulting compound | |
|---|---|---|---|
| Example | Mercaptan | R | Mp (° C) |
| 2 A | ethyl mercaptan | $CH_2CH_3$ | 167–168 |
| 3 A | 2-hydroxyethyl mercaptan | $CH_2CH_2OH$ | 192–194 |
| 4 A | 2-aminoethyl mercaptan | $CH_2CH_2NH_2$ | 188–191 |
| 5 A | allyl mercaptan | $CH_2CH_2=CH_2$ | 167–170 |
| 6 A | isobutyl mercaptan | $CH_2CH(CH_3)_2$ | 104–112 |
| 7 A | sec-butyl mercaptan | $CH(CH_3)CH_2CH_3$ | 150–157 |
| 8 A | cyclopentyl mercaptan | cyclopentyl | 100–109 |
| 9 A | mercaptoacetic acid methyl ester | $CH_2COOCH_3$ | 125–129 |
| 10 A | furfuryl mercaptan | furfuryl | 146–148 |

16β-Thioethers of 16-deacetoxyfusidic acid

By following the procedure of Example 1 B and substituting the 16β-thioethers of 3-O-acetyl-16-deacetoxyfusidic acid p-nitrobenzyl ester listed in table VII for 3-O-acetyl-16-deacetoxy-16β-isopropylthiofusidic acid p-nitrobenzyl ester, the 16β-thioethers of 16-deacetoxyfusidic acid indicated in table VIII were prepared.

Table VIII:

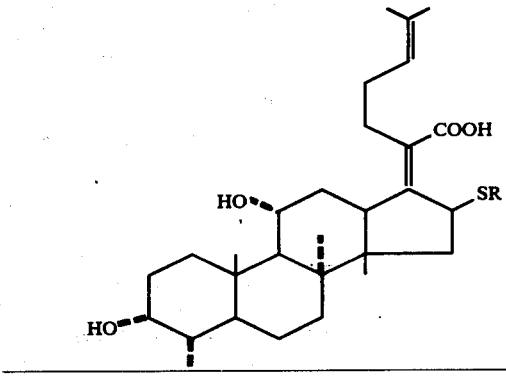

| | Resulting compounds | |
|---|---|---|
| Example | R | Mp (° C) |
| 2 B | $CH_2CH_3$ | 195–198 |
| 3 B | $CH_2CH_2OH$ | 179–182 |
| 4 B | $CH_2CH_2NH_2$ | 241–250 (dec) |

Table VIII:-continued

| | Resulting compounds | |
|---|---|---|
| Example | R | Mp (° C) |
| 5 B | $CH_2CH=CH_2$ | 196–199 |
| 6 B | $CH_2CH(CH_3)_2$ | 199–202 |
| 7 B | $CH(CH_3)CH_2CH_3$ | 218–222 |
| 8 B | cyclopentyl | 217–223 |
| 9 B | $CH_2COOH$ | 199–202 |
| 10 B | furfuryl | amorphous |

The NMR spectrum (CDCl₃) of the compound of Example 10 B shows signals at δ = 0.97 (s, 6H), 1.32 (s, 3H), 1.60 and 1.68 (2 bs, 6H), 3.00 (m, 1H; C$\underline{H}$-13), 3.73 (m, 1H; C$\underline{H}$-3), 3.78 (bs, 2H; SC$\underline{H}_2$), 4.22 (d, 1H, C$\underline{H}$-16), 4.30 (m, 1H; C$\underline{H}$-11), 5.10 (m, 1H; C$\underline{H}$-24), 6.1–6.4 (m, 2H; arom. C$\underline{H}$) and 7.32 (bs, 1H; arom. C$\underline{H}$) ppm. Tetramethylsilane was used as internal reference.

EXAMPLE 11

16-Deacetoxy-16β-isopropylthio-24,25-dihydro-fusidic acid

A.

3-O-Acetyl-16-deacetoxy-16β-isopropylthio-24,25-dihydrofusidic acid p-nitrobenzyl ester By following the procedure of Example 1 A and substituting 3-O-acetyl-16-deacetoxy-16α-bromo-24,25-dihydrofusidic acid p-nitrobenzyl ester for 3-O-acetyl-16-deacetoxy-16α-bromofusidic acid p-nitrobenzyl ester, 3-O-acetyl-16-deacetoxy-16β-isopropylthio-24,25-dihydrofusidic acid p-nitrobenzyl ester was prepared as colourless crystals, melting point 113°–116° C.

B.

16-Deacetoxy-16β-isopropylthio-24,25-dihydrofusidic acid

By following the procedure of Example 1 B and substituting 3-O-acetyl-16-deacetoxy-16β-isopropylthio-24,25-dihydrofusidic acid p-nitrobenzyl ester for 3-O-acetyl-16-deacetoxy-16β-isopropylthiofusidic acid p-nitrobenzyl ester, 16-deacetoxy-16β-isopropylthio-24,25-dihydrofusidic acid was prepared, melting point 232°–234° C.

EXAMPLE 12

16-Deacetoxy-16β-cyclohexylthiofusidic acid

3-O-Acetyl-16-deacetoxy-16α-bromofusidic acid p-nitrobenzyl ester (1.43 g; 2 mmol) was added to a solution of potassium hydroxide (400 mg of 85% purity; 6.1 mmol) and cylcohexyl mercaptan (2 ml, 16 mmol) in ethanol (100 ml), and the resulting solution was left at room temperature for five days. Thereafter, the reaction mixture was diluted with 150 ml of ether, washed with water (3 × 75 ml), dried and evaporated in vacuo. The residual oil, containing the crude 3-O-acetyl-16-deacetoxy-16β-cyclohexylthiofusidic acid p-nitrobenzyl ester, was dissolved in ethanol (80 ml), and 20 ml of 2 N aqueous sodium hydroxide was added. After stirring for 3 hours at 60° C, 100 ml of water was added, and the resulting dark solution was acidified with 4 N hydrochloric acid (15 ml) and extracted twice with ether. The combined organic phases were washed with water (3 × 50 ml), dried and evaporated. The oily residue was purified by dry column chromatography on silica gel (ether-petroleum ether-acetic acid; 70:30:0.5) to give 16-deacetoxy-16β-cyclohexylthiofusidic acid, crystallized from ether-petroleum ether, melting point: 215°–220° C. Recrystallization from ethyl acetate-petroleum ether gave the analytically pure compound, melting point: 216°–220° C.

EXAMPLES 13–15

Following the procedure of Example 12 and substituting the mercaptans listed in table IX for cyclohexyl mercaptan, the 16β-thioethers of 16-deacetoxyfusidic acid indicated in table IX were prepared.

Table IX

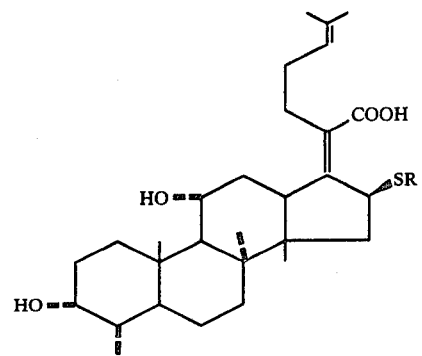

| Ex. | Mercaptan | Resulting compound R | Mp (° C) |
|---|---|---|---|
| 13 | 2-phenylethyl mercaptan | $CH_2CH_2C_6H_5$ | 208–214 |
| 14 | n-butyl mercaptan | $CH_2CH_2CH_2CH_3$ | 105–118 (dec) |
| 15 | methyl mercaptan | $CH_3$ | amorphous |

The NMR spectrum (CD$_3$OD) of the compound of Example 15 shows signals at δ = 0.89 (d, J=6, 3H), 1.00 (s, 3H), 1.03 (s, 3H), 1.38 (s, 3H), 1.62 (bs, 6H), 2.13 (s, 3H; SC$\underline{H}_3$), 3.03 (m, 1$\underline{H}$; CH-13), 3.67 (m, 1H; C$\underline{H}$-3), 4.03 (d, J=9, 1H; C$\underline{H}$-16), 4.26 (m, 1H; C$\underline{H}$-11) and 5.10 (m, 1H; C$\underline{H}$-24) ppm. Tetramethylsilane was used as internal reference.

EXAMPLE 16

16-Deacetoxy-16β-ethylthiofusidic acid

To a solution of ethyl mercaptan (2.5 ml; 34 mmol) in dimethylformamide (10 ml) was added sodium hydride (650 mg of a 55% suspension in oil; 15 mmol). When the evolution of hydrogen ceased, 3-O-acetyl-16-deacetoxy-16α-bromofusidic acid pivaloyloxymethyl ester (750 mg, 1.1 mmol) was added. After standing one hour at room temperature, the reaction mixture was diluted with ethyl acetate (50 ml) and extracted with 1 N hydrochloric acid (25 ml) and water (2 × 25 ml). The organic phase was dried, filtered and evaporated in vacuo. The crude product thus obtained was purified by dry column chromatography on silica gel (ether:petroleum ether:acetic acid; 40:60:0.5) and afforded pure 3-O-acetyl-16-deacetoxy-16β-ethylthiofusidic acid as a colourless gum, which was dissolved in a mixture of ethanol (20 ml) and 2 N aqueous sodium hydroxide (5 ml) and left at 75° C for 2 hours. The reaction mixture was then acidified with 1 N hydrochloric acid (15 ml) and extracted with ethyl acetate (50 ml). The organic phase was washed twice with water (20 ml), dried, and evaporated in vacuo to give an oil, which was crystallized from ether-petroleum ether to yield 16-deacetoxy-16β-ethylthiofusidic acid as colourless crystals, melting point: 195°–198° C.

EXAMPLES 17–20

16-β-Thioethers of 16-deacetoxyfusidic acid

Following the procedure of Example 16 and substituting the mercaptans listed in table X for ethyl mercaptane, the 16β-thioethers of 16-deacetoxyfusidic acid shown in table X were prepared.

Table X:

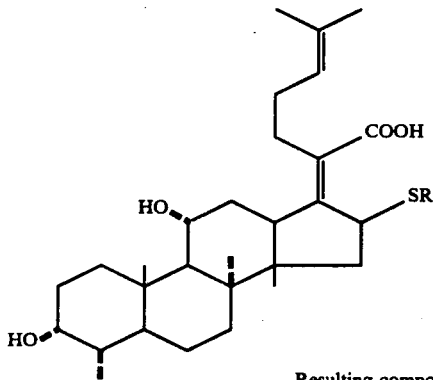

| Example | Mercaptan | Resulting compound R | Mp (° C) |
|---|---|---|---|
| 17 | n-propyl mercaptan | $CH_2CH_2CH_3$ | amorphous |
| 18 | t-butyl mercaptan | $C(CH_3)_3$ | 200–203 |
| 19 | phenyl mercaptan | $C_6H_5$ | amorphous |
| 20 | benzyl mercaptan | $CH_2C_6H_5$ | amorphous |

The NMR spectrum (CD$_3$OD) of the compound of Example 17 shows signals at δ = 0.90 (d, 3H), 0.99 (s, 6H), 1.37 (s, 3H), 1.62 and 1.66 (2 bs, 6H), 2.58 (m, 2H; C$\underline{H}_2$S), 3.00 (m, 1H; C$\underline{H}$-13), 3.67 (m,1H; CH-3), 4.11 (d, 1H; C$\underline{H}$-16), 4.24 (m, 1H; C$\underline{H}$-11) and 5.12 (m, 1H; C$\underline{H}$-24) ppm. Tetramethylsilane was used as internal reference.

The NMR spectrum (CDCl$_3$) of the compound of Example 19 shows signals at δ = 0.95 (s, 6H), 1.10 (s, 3H), 1.35 (s, 3H), 1.60 and 1.65 (2bs, 6H), 3.10 (m, 1H; C$\underline{H}$-13), 3.74 (m, 1H; C$\underline{H}$-3), 4.30 (m, 1H; C$\underline{H}$-11), 4.77 (d, 1H; C$\underline{H}$-16), 5.11 (m, 1H; C$\underline{H}$-24) and 7.0-7.4 (5H; arom. C$\underline{H}$) ppm. Tetramethylsilane was used as internal reference.

The NMR spectrum (CDCl$_3$) of the compound of Example 20 shows signals at δ = 0.97 (s, 6H), 1.36 (s, 3H), 1.62 and 1.66 (2 bs; 6H), 3.06 (m, 1H; C$\underline{H}$-13), 3.66 (m, 1H; C$\underline{H}$-3), 3.74 (bs, 2H; SC$\underline{H}_2$), 4.08 (d, 1H; C$\underline{H}$-16), 4.24 (m, 1H; C$\underline{H}$-11), 5.14 (m, 1H; C$\underline{H}$-24) and 7.3 (bs, 5H; arom. C$\underline{H}$) ppm. Tetramethylsilane was used as internal reference.

EXAMPLE 21

16-Deacetoxy-16β-(1'-methyltetrazol-5'-ylthio)fusidic acid

16-Epideacetylfusidic acid benzoyloxymethyl ester (2.2 g; 3.4 mmol) and di(1-methyltetrazol-5-yl)disulfide (1.5 g; 6.5 mmol) was dissolved in dry pyridine (20 ml). The solution was cooled in an ice-bath and tributylphosphine (1.44 ml; 6 mmol) was added. After standing for 18 hours at room temperature, water (200 ml) and ether (400 ml) was added to the reaction mixture. The organic phase was separated, washed twice with 1 N hydrochloric acid and twice with water, dried, and evaporated in vacuo. The residue was dissolved in methanol (50 ml), and potassium carbonate (2.4 g; 17.5 mmol) was added. After stirring for 18 hours at room temperature, the solution was acidified with 4 N aqueous hydrochloric acid (8 ml), and water (200 ml) and ether (100 ml) was added. The organic phase was separated, washed twice with water, dried, and evaporated to give 1.84 g of crude product, which was purified by dry column chromatography on silica gel (ether:acetic acid; 100:0.5) to yield 800 mg of 16-deacetoxy-16β-(1'-methyltetrazol-5'-ylthio)fusidic acid as a colourless foam. The nmr spectrum (CDCl$_3$) shows signals at δ = 1.00 (s, 3H), 1.06 (s, 3H), 1.40 (s, 3H), 1.62 and 1.68 (2 bs, 6H), 3.17 (m, 1H; C$\underline{H}$-13), 3.75 (m, 1H; C$\underline{H}$-3), 3.87 (s, 3H; 1'-C$\underline{H}_3$), 4.37 (m, 1H, C$\underline{H}$-11) and 5.42 (m, 1H; C$\underline{H}$-16) ppm. Tetramethylsilane was used as internal reference.

EXAMPLE 22

16-Deacetoxy-16β-(2',5'-dichloro-phenylthio)fusidic acid

A solution of 3-O-acetyl-16-epideacetylfusidic acid methoxymethyl ester (490 mg; 0.87 mmol) and di(2,5-dichlorophenyl)disulfide (1.07 g; 3.75 mmol) in dry pyridine (4 ml) was cooled to 0° C, and tributylphosphine (0.72 ml; 3.0 mmol) was added. The resuling solution was left at 5° C for 3 days and then diluted with ether (100 ml), washed with 4 N hydrochloric acid, 2 N sodium hydroxide and water, dried, and evaporated in vacuo. The residue was dissolved in a mixture of ethanol (20 ml) and 2 N aqueous sodium hydroxide (8 ml), and kept at 60° C for 1 hour. The reaction mixture was then acidified with 4 N hydrochloric acid (5 ml), and ether (100 ml) and water (200 ml) was added. The organic phase was separated, washed twice with water, dried and evaporated in vacuo. The residue was crystalized from ether-petroleum ether to give 16-deacetoxy-16β-(2',5'-dichlorophenylthio)fusidic acid, melting point 161°-164° C.

EXAMPLE 23

16-Deacetoxy-16β-(2'-azidoethylthio)fusidic acid

A.

3-O-Acetyl-16-deacetoxy-16β-(2'-bromoethylthio)-fusidic acid p-nitrobenzyl ester To a solution of 3-O-acetyl-16-deacetoxy-16β-(2'-hydroxyethylthio)fusidic acid p-nitrobenzyl ester (1 g; 1.4 mmol) in 50 ml of dimethylformamide was added 3 g of phenyl N,N-dimethylformimidate bromide. After standing at room temperature for 18 hours, the reaction mixture was diluted with ether (50 ml), washed with 2 N sodium hydroxide (20 ml) and water (3 × 50 ml), dried, and evaporated in vacuo. Addition of ether-petroleum ether caused the residue to crystallize. The product was filtered off, washed with petroleum ether, and dried to yield 800 mg of 3-O-acetyl-16-deacetoxy-16β-(2'-bromoethylthio)fusidic acid p-nitrobenzyl ester, melting point 148°-150° C.

B. 16-Deacetoxy-16β-(2'-azidoethylthio)fusidic acid

The 2'-bromoethylthioether prepared above was dissolved in 25 ml of dimethylformamide, lithium azide (400 mg; 8.2 mmol) was added, and the reaction mixture was left at 20° C for 24 hours. 100 ml of ether was then added, and the resulting solution was washed with water (4 × 50 ml), dried, and evaporated in vacuo. The residue was dissolved in a mixture of ethanol (50 ml) and 2 N aqueous sodium hydroxide and after being left at 60° C for 3 hours, the solution was acidified with 8 ml of 4 N hydrochloric acid, and water (100 ml) and ether (100 ml) was added. The organic phase was separated, washed with water (4 × 50 ml), dried, and evaporated in vacuo. Addition of ether and petroleum ether to the residue caused 16-deacetoxy-16β-(2'-azidoethylthio)-fusidic acid to precipitate as colourless crystals, which were filtered off, washed with petroleum ether, and dried to yield 140 mg, melting point 173°-179° C.

EXAMPLE 24

16-Deacetoxy-16β-(2'-methyoxyethylthio)fusidic acid sodium salt

To a solution of 3-O-acetyl-16-deacetoxy-16β-(2'-bromoethylthio)fusidic acid p-nitrobenzyl ester (see Example 23 A for the preparation of this compound) (1 g; 1.3 mmol) in methanol (50 ml) was added silver carbonate (1 g; 3.6 mmol), and the mixture was stirred at room temperature for 16 hours. The insoluble material was filtered off and washed with methanol (10 ml). The combined filtrate and washing were evaporated in vacuo, and the residue was dissolved in a mixture of ethanol (100 ml) and 2 N sodium hydroxide (20 ml). After stirring for 3 hours at 60° C, the dark solution was acidified with 4 N hydrochloric acid (15 ml), and water (200 ml) and ether (200 ml) was added. The organic phase was separated, washed twice with water, dried and evaporated in vacuo. The residue was purified by dry column chromatography on silica gel (ether:acetic acid; 100:0.5) to give the desired product as a colourless foam, which was converted into a crystalline sodium salt by dissolving in methanol (25 ml), titrating with 2 N aqueous sodium hydroxide, evaporating, and adding acetone. The crystals were filtered off, washed with acetone, and dried to yield 16-deacetoxy-16β-(2'-methoxyethylthio)fusidic acid sodium salt.

The NMR spectrum (CD$_3$OD) shows signals at δ = 1.00 (s, 6H), 1.36 (s, 3H), 1.62 (bs, 6H) 2.78 (2H, C$\underline{H}_2$S), 3.51 (2H; C$\underline{H}_2$O), 3.68 (m, 1H; C$\underline{H}$-3), 4.10 (d, 1H; C$\underline{H}$-16), 4.21 (m, 1H; C$\underline{H}$-11) and 5.11 (m, 1H; C$\underline{H}$-24) ppm. Tetramethylsilane was used as internal reference.

EXAMPLE 25

16-Deacetoxy-16β-(2'-isopropylthioethylthio)fusidic acid

To a solution of potassium hydroxide (500 mg; 9 mmol) and isopropyl mercaptan (1.5 ml; 16 mmol) in ethanol (50 ml) was added 3-O-acetyl-16-deacetoxy-16β-(2'-bromoethylthio)fusidic acid p-nitrobenzylester (see Example 23A for the preparation of this compound) (1 g; 1.3 mmol), and the mixture was stirred for 16 hours at room temperature. Water (100 ml) and ether (75 ml) was added, the organic phase was separated, washed with 2 N sodium hydroxide (2 × 25 ml) and water (2 × 25 ml), dried, and evaporated in vacuo. The residue was dissolved in a mixture of ethanol (100 ml) and 2 N sodium hydroxide (20 ml), and the solution stirred for 3 hours at 60° C. 4 N hydrochloric acid (15 ml), water (250 ml) and ether (100 ml) was added, the organic phase was separated, washed with water (2 × 50 ml), dried, and evaporated in vacuo. The desired product was isolated from the residue by dry column chromatography (ether:petroleum ether:acetic acid, 70:30:0.5) to yield 400 mg of 16-deacetoxy-16β-(2'-isopropylthioethylthio)fusidic acid as a colourless foam.

The nmr spectrum (CDCl$_3$) shows signals at δ = 0.96 (bs, 6H), 1.22 (d, J=7, 6H), 1.33 (s, 3H), 1.58 and 1.67 (2bs, 6H), 2.73 (bs, 4H; SC$\underline{H}_2$C$\underline{H}_2$S), 2.91 (m, 1H; S-C$\underline{H}$(CH$_3$)$_2$), 3.01 (m, 1h, C$\underline{H}$-13), 3.71 (m, 1H; C$\underline{H}$-3), 4.21 (m, 1H; C$\underline{H}$-16), 4.28 (m, 1H; C$\underline{H}$-11) and 5.08 (m, 1H, C$\underline{H}$-24) ppm. Tetramethylsilane was used as internal reference.

EXAMPLE 26-28

By following the procedure described in Example 25 and substituting the mercaptans listed in table XI for isopropyl mercaptan, the compounds indicated in table XI were prepared Table XI:

| Example | Mercaptan | R | Mp (° C) |
|---|---|---|---|
| 26 | ethyl mercaptan | CH$_2$CH$_3$ | 149-152 |
| 27 | t-butyl mercaptan | C(CH$_3$)$_3$ | 134-135 |
| 28 | cyclohexyl mercaptan | cyclohexyl | amorphous |

The NMR spectrum of the compound of Example 28 (CDCl$_3$) shows signals at δ = 0.99 (s, 6H), 1.37 (s, 3H), 1.61 and 1.68 (2bs, 6H), 2.78 (bs, 4H; SC$\underline{H}_2$C$\underline{H}_2$S), 3.07 (m, 1H; C$\underline{H}$-13), 3.76 (m, 1H; C$\underline{H}$-3), 4.26 (d, 1H; C$\underline{H}$-16), 4.35 (m, 1H; C$\underline{H}$-11) and 5.12 (m, 1H; C$\underline{H}$-24) ppm. Tetramethylsilane was used as internal reference.

EXAMPLE 29

16-Deacetoxy-16β-(2'-phenylthioethylthio)fusidic acid

To an ice-cooled solution of 3-O-acetyl-16-deacetoxy-16β-(2'-hydroxyethylthio)fusidic acid p-nitrobenzyl ester (1 g; 1.4 mmol) and diphenyldisulfide (1 g; 4.6 mmol) in dry pyridine (7 ml) was added tributylphosphine (2 ml; 8.4 mmol), and the mixture was left at 5° C for 16 hours. Ether (100 ml) was added, and the resulting solution was washed with 4 N hydrochloric acid (2 × 25 ml), 2 N sodium hydroxide (2 × 25 ml) and water (2 × 25 ml), dried, and evaporated in vacuo. The residue was dissolved in a mixture of ethanol (90 ml) and 2 N sodium hydroxide (20 ml). After stirring for 3 hours at 60° C, 4 N hydrochloric acid (15 ml), water (200 ml) and ether (100 ml) was added. The organic phase was separated, washed with water (2 × 20 ml), and evaporated in vacuo. The residue was purified by dry column chromatography on silica gel (ethyl acetate:cyclohexane; 1:1) to yield 630 mg of 16-deacetoxy-16β-(2'-phenylthioethylthio)fusidic acid as a colourless foam.

The nmr spectrum (CDCl$_3$) shows signals at δ = 0.98 (bs, 6H), 1.35 (s, 3H), 1.61 and 1.67 (2 bs, 6H), 3.78 (m, 1H; C$\underline{H}$-3), 4.25 (m, 1H; C$\underline{H}$-16), 4.34 (m, 1H; C$\underline{H}$-11), 5.11 (m, 1H; C$\underline{H}$-24) and 7.1-7.5 (m, 5H; arom. C$\underline{H}$) ppm. Tetramethylsilane was used as internal reference.

EXAMPLE 30

Sodium salt of 16-deacetoxy-16β-(2'-methylthioethylthio)fusidic acid

To an ice-cooled solution of 3-O-acetyl-16-deacetoxy-16β-(2'-hydroxyethylthio)fusidic acid p-nitrobenzyl ester (1 g; 1.4 mmol) in 1 ml of dimethyldisulfide (∼ 10 mmol) was added tributylphosphine (2 ml; 8.4 mmol), and the mixture was left at 20° C for 3 days. Ether (100 ml) was then added, and the resulting solution was washed with 2 N sodium hydroxide (25 ml)

and water (2 × 25 ml), dried, and evaporated in vacuo. The residue was dissolved in a mixture of ethanol (40 ml) and 2 N sodium hydroxide (10 ml). After stirring for 3 hours at 60° C, 4 N hydrochloric acid (10 ml), water (200 ml), and ether (100 ml) was added. The organic phase was separated, washed with water (3 × 20 ml), and evaporated in vacuo. The residue was purified by dry column chromatography on silica gel (ether:petroleum ether:acetic acid; 70:30:0.5) to yield 410 mg of 16-deacetoxy-16β-(2'-methylthioethylthio)fusidic acid as a colourless oil. The crystalline sodium salt was prepared by dissolving this oil in methanol (10 ml), titrating with 2 N aqueous sodium hydroxide using phenolphthalein as indicator, evaporating in vacuo, and adding acetone. The crystals were filtered off and washed with acetone and ether to yield the pure sodium salt of 16-deacetoxy-16β-(2'-methylthioethylthio)fusidic acid.

The NMR spectrum (CD$_3$OD) shows signals at δ = 0.98 (s, 6H), 1.36 (s, 3H), 1.62 (bs, 6H), 2.10 (s, 3H; SC$\underline{H}_3$), 2.77 (bs, 4H; SC$\underline{H}_2$C$\underline{H}_2$S), 3.00 (m, 1H; C$\underline{H}$-13), 3.66 (m, 1H; C$\underline{H}$-3), 4.11 (d, 1H; C$\underline{H}$-16), 4.23 (m, 1H; C$\underline{H}$-11) and 5.13 (m, 1H; C$\underline{H}$-24) ppm. Tetramethylsilane was used as internal reference.

EXAMPLE 31

16-Deacetoxy-16β-(2'-fluoroethylthio)fusidic acid

A.

3-O-Formyl-16-deacetoxy-16β-(2'-bromoethylthio)-fusidic acid benzoyloxymethyl ester 16-Deacetoxy-16β-(2'-hydroxyethylthio)fusidic acid (53.4 mg; 1 mmol) was dissolved in methanol (10 ml) and converted into its sodium salt by titration with 2 N sodium hydroxide using phenolphthalein as indicator. After evaporation in vacuo, the resulting amorphous sodium salt was dissolved in dimethylformamide (7.5 ml), chloromethylbenzoate (0.16 ml; 1 mmol) was added, and the mixture was stirred at room temperature for 48 hours. Water (50 ml) was added, and the mixture was extracted with ether (100 ml). The organic phase was separated, washed with water (4 × 100 ml), dried and evaporated in vacuo to yield 16-deacetoxy-16β-(2'-hydroxyethylthio)fusidic acid benzoyloxymethyl ester as an amorphous product. This was dissolved in dimethylformamide (10 ml), phenyl N,N-dimethylformimidate bromide (1.5 g; ca. 6.5 mmol) was added with stirring, and the solution was kept at 20° C for 24 hours. Water (50 ml) and ether (50 ml) was added, and the organic phase was washed with 2 N sodium hydroxide (2 × 25 ml) and water (2 × 25 ml), dried, and evaporated in vacuo to give 3-O-formyl-16-deacetoxy-16β-(2'-bromoethylthio)fusidic acid benzoyloxymethyl ester as an amorphous product.

B. 16-Deacetoxy-16β-(2'-fluoroethylthio)fusidic acid

The 2'-bromoethylthioether prepared above was dissolved in acetonitrile (25 ml), silver fluoride (500 mg) was added, and the resulting suspension was stirred at room temperature for 2 hours. Ethyl acetate (50 ml) was added, and the insoluble material was filtered off. The filtrate was evaporated in vacuo, the residue was dissolved in methanol (10 ml), and potassium carbonate (350 mg; 2.5 mmol) was added. After stirring for 30 minutes at room temperature, water (100 ml), 4 N hydrochloric acid (5 ml) and ether (100 ml) was added, and the organic phase was separated, washed twice with water, dried, and evaporated to yield an amorphous product, which was purified by dry column chromatography (ether:acetic acid; 100:0.5) to yield pure 16-deacetoxy-16β-(2'-fluoroethylthio)fusidic acid, crystallized from ether-petroleum ether, melting point 157°–159° C.

EXAMPLE 32

11-Keto-16-deacetoxy-16β-isopropylthiofusidic acid

A.

3-O-Acetyl-11-keto-16-deacetoxy-16β-isopropylthiofusidic acid p-nitrobenzyl ester Pyridinium chlorochromate (1.07 g, 5 mmol) was suspended in methylene chloride (30 ml) by stirring, while 3-O-acetyl-16-deacetoxy-16β-isopropylthiofusidic acid p-nitrobenzyl ester (1.5 g, 2.1 mmol) was rapidly added. After stirring for an additional hour, the suspension was diluted with ether (100 ml), the solvent was decanted, and the black solid was washed twice with ether. Filtration and evaporation of the combined organic extracts yielded an oily residue, which crystallized from ether-petroleum ether. The colourless crystals thus obtained were collected, washed with petroleum ether, and dried to afford 880 mg of the desired product, melting point 120°–122° C.

B. 11-Keto-16-deacetoxy-16β-isopropylthiofusidic acid

The p-nitrobenzyl ester prepared above was dissolved in a mixture of ethanol (20 ml) and 2 N aqueous sodium hydroxide (5 ml) and heated to 60° C for 3 hours. Then, 4 N hydrochloric acid (3 ml), water (100 ml) and ether (100 ml) was added with stirring. The organic phase was separated, washed twice with water (25 ml), dried, and evaporated in vacuo. The resulting oily residue was purified by dry column chromatography on silica gel (cyclohexane:ethyl acetate, 7:3) to yield 380 mg of 11-keto-16-deacetoxy-16β-isopropylthiofusidic acid, melting point 167°–169° C (crystallized from ether-petroleum ether).

EXAMPLE 33

11-Keto-16-deacetoxy-16β-isopropylthio-24,25-dihydrofusidic acid

By following the procedure of Example 32 and substituting 3-O-acetyl-16-deacetoxy-16β-isopropylthio-24,25-dihydrofusidic acid p-nitrobenzyl ester for 3-O-acetyl-16-deacetoxy-16β-isopropylthiofusidic acid p-nitrobenzyl ester, 11-keto-16-deacetoxy-16β-isopropylthio-24,25-dihydrofusidic acid was prepared as colourless crystals, melting point 189°–191° C.

EXAMPLE 34

3-Keto-16-deacetoxy-16β-isopropylthiofusidic acid

To a solution of 16-deacetoxy-16β-isopropylthiofusidic acid acetoxymethyl ester (2.0 g, 3.3 mmol) in 15 ml of dimethylsulfoxide was added dicyclohexylcarbodiimide (3.10 g, 15 mmol) and orthophosphoric acid (160 mg, 2 mmol), and the mixture was left with stirring at room temperature for 24 hours. A solution of oxalic acid (3 g) in methanol (20 ml) was then added to destroy excess of carbodiimide, and stirring was continued for 30 minutes. Ethyl acetate (150 ml) was then added, and the resulting solution was washed with saturated aqueous sodium hydrogen carbonate (2 × 50 ml) and water (50 ml), dried, and evaporated to yield 1.9 g of an oily residue. This was dissolved in methanol (40 ml) and potassium carbonate (1.2 g) was added. After stirring for one hour, the methanol was evaporated in vacuo, and ether (100 ml) and 4 N hydrochloric acid (50 ml) were added to the residue. The organic phase was washed with water (2 × 50 ml), dried, and evaporated in vacuo. The oily residue was purified by dry column chromatography on silica gel (cyclohexane:ethyl acetate, 7:3) to yield 3-keto-16-deacetoxy-16β-isopropylthiofusidic acid as colourless crystals, collected from ether, melting point 200°–203° C.

EXAMPLE 35

16-Deacetoxy-16β-isopropylsulfinylfusidic acid

Sodium metaperiodate (6 g; 28 mmol) in 500 ml of water was added to a solution of 16-deacetoxy-16β-isopropylthiofusidic acid (10.0 g; 18.3 mmol) in a mixture of methanol (200 ml) and 2 N aqueous sodium hydroxide (10 ml). After standing for 1.5 hours, the resulting solution was acidified with 4 N aqueous hydrochloric acid (7.5 ml), causing a crystalline product to precipitate. The crystals were filtered off, washed with water (50 ml), and dried to yield 10.0 g of the desired product, mp. 158°–159° C. The crystals thus obtained were transformed into another crystal modification by treating with boiling ethyl acetate (400 ml). After cooling to 0° C, the product was filtered off washed with ether (50 ml), and dried to afford 9.04 g of pure 16-deacetoxy-16β-isopropylsulfinylfusidic acid, melting point 179°–181° C.

EXAMPLE 36–41

By following the procedure described in Example 35 and substituting the 16β-thioethers of 16-deacetoxyfusidic acid listed in table XII for 16-deacetoxy-16β-isopropylthiofusidic acid, the sulfoxides indicated in table XII were prepared Table XII

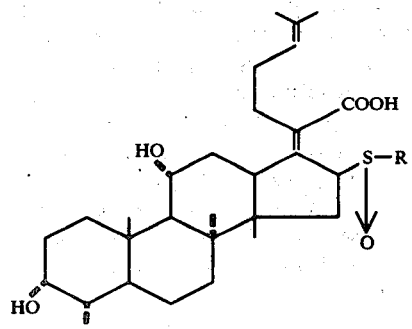

| Example | thioether of 16-deacetoxy fusidic acid | R | Mp (° C) |
|---|---|---|---|
| 36 | 16β-methylthioether | CH₃ | 151–156 |
| 37 | 16β-ethylthioether | CH₂CH₃ | 158–162.5 |
| 38 | 16β-t-butylthioether | C(CH₃)₃ | 164–167 |
| 39 | 16β-(2'-hydroxyethylthio)ether | CH₂CH₂OH | 163–168 |
| 40 | 16β-(2'-azidoethylthio)ether | CH₂CH₂N₃ | 141–147 |
| 41 | 16β-phenylthioether | C₆H₅ | amorphous |

EXAMPLE 42

16-Deacetoxy-16β-isopropylsulfinyl-24,25-dihydrofusidic acid

By following the procedure described in Example 35 and substituting 16-deacetoxy-16β-isopropylthio-24,25-dihydrofusidic acid for 16-deacetoxy-16β-isopropylthiofusidic acid, 16-deacetoxy-16β-isopropylsulfinyl-24,25-dihydrofusidic acid was prepared as colourless crystals, melting point 184°–186° C.

EXAMPLE 43

16-Deacetoxy-3-keto-16β-isopropylsulfinylfusidic acid

By following the procedure described in Example 35 and substituting 16-deacetoxy-3-keto-16β-isopropylthiofusidic acid for 16-deacetoxy-16β-isopropylthiofusidic acid, 16-deacetoxy-3-keto-16β-isopropylsulfinylfusidic acid was prepared as colourless crystals, melting point 158°–161° C.

EXAMPLE 44

11-Keto-16-deacetoxy-16β-isopropylsulfinylfusidic acid

To a solution of 16-deacetoxy-16β-isopropylsulfinylfusidic acid (1.1 g; 2 mmol) in 5 ml of pyridine was added acetic anhydride (0.8 ml; 8.5 mmol). After standing for 48 hours at room temperature, 1 ml of water was added to the solution, which after an additional hour was diluted with 50 ml of ethyl acetate, washed twice with 4 N hydrochloric acid and twice with water, dried, and evaporated to give 940 mg of crystalline 3-O-acetyl-16-deacetoxy-16β-isopropylsulfinylfusidic acid collected from ether, melting point 176°–178° C.

To a suspension of 770 mg of this product in acetone (100 ml) was added Jones reagent (0.78 ml). After standing for 10 minutes at room temperature, water (100 ml) was added to the reaction mixture, and the resulting solution was concentrated in vacuo to 125 ml causing 3-O-acetyl-11-keto-16-deacetoxy-16β-isopropylsulfinylfusidic acid to precipitate as colourless crystals, which were filtered off, washed with water and dried to yield 570 mg; melting point 151°–160° C.

400 mg of this product was dissolved in a mixture of ethanol (20 ml) and 2 N aqueous sodium hydroxide (2 ml), and left at room temperature for 6 days. 4 N aqueous hydrochloric acid (2 ml) was then added with stirring to precipitate the desired product as colourless crystals, which were collected, washed with water (15 ml), and dried to afford 230 mg, melting point 174°–178° C.

Recrystallization from ethyl acetate gave the pure 11-keto-16-deacetoxy-16β-isopropylsulfinylfusidic acid, melting point 181°–183° C.

EXAMPLE 45

3,11-Diketo-16-deacetoxy-16β-isopropylsulfinylfusidic acid

To a solution of 16-deacetoxy-16β-isopropylthiofusidic acid (500 mg; 0.94 mmol) in 100 ml of acetone was added 1.6 ml of Jones reagent. After standing at room temperature for 10 minutes, 100 ml of water was added with stirring to the reaction mixture. The white precipitate which formed was filtered off, washed with water and dried to give 450 mg of a mixture of 3,11-diketo-16-deacetoxy-16β-isopropylthiofusidic acid and the desired product.

The crystals were dissolved in hot ether (20 ml) and upon cooling to 0° C pure 3,11-diketo-16-deacetoxy-16β-isopropylsulfinylfusidic acid precipitated. The crystals were filtered off, washed with cold ether and dried to give 60 mg, melting point 154°-162° C.

EXAMPLE 46

16-Deacetoxy-16β-ethoxyfusidic acid

Silver carbonate (16.55 g; 60 mmol) was added to a suspension of 3-O-acetyl-16-deacetoxy-16α-bromofusidic acid phenacyl ester (20.94 g; 30 mmol) in ethanol (300 ml), and, after being protected from light, the mixture was stirred at room temperature for 18 hours. Insoluble material was filtered off and washed with ethanol (2 × 30 ml). To the combined filtrate and washings was added 5 N aqueous sodium hydroxide (120 ml), and the mixture was refluxed for two hours. After cooling to room temperature, the major part of ethanol was removed in vacuo, and to the residue was added ethyl acetate (150 ml) and water (100 ml). The stirred mixture was acidified with 4 N hydrochloric acid, the organic phase was separated, and the aqueous phase reextracted with ethyl acetate (50 ml). The combined organic extracts were washed with water, dried, and evaporated in vacuo to yield an oily residue, which crystallized from diisopropyl ether. The colourless crystals thus obtained were collected, washed with diisopropyl ether, and dried to afford 5.42 g of 16-deacetoxy-16β-ethoxyfusidic acid, melting point: 169°-171° C. After work-up of the mother liquor, a further 2.20 g of the desired compound, melting point: 168°-170° C, was obtained. Two recrystallizations from methanol-diisopropyl ether gave the analytically pure compound, melting point: 177°-178° C.

EXAMPLES 47-49

16-Deacetoxy-16β-alkyloxyfusidic acids

By substituting the alcohols listed in table XIII for the ethanol in the procedure of Example 46, the 16-deacetoxy-16β-alkyloxyfusidic acids indicated in table XIII were obtained.

Table XIII

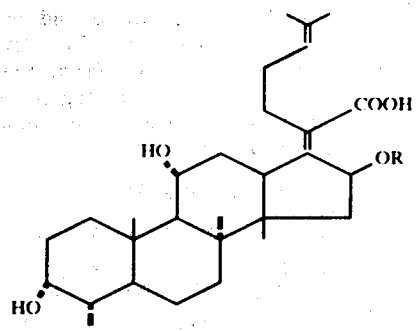

| Example | Alcohol | Resulting compound R | Mp (° C) |
|---|---|---|---|
| 47 | Methanol | $CH_3$ | 175-176 |
| 48 | 2,2,2-Trifluoroethanol | $CH_2CF_3$ | 202-203 |
| 49 | Hexanol-(1) | $CH_2(CH_2)_4CH_3$ | amorphous |

EXAMPLE 50

16-Deacetoxy-16β-(2'-fluoroethoxy)fusidic acid

To a solution of 3-O-formyl-16-deacetoxy-16α-bromofusidic acid benzoyloxymethyl ester (8.75 g; 12.5 mmol) in 2-fluoroethanol (25 ml) was added silver carbonate (6.89 g; 25 mmol), and the mixture was stirred at room temperature and in the absence of light for 16 hours. The insoluble material was filtered off, washed twice with ether, and the combined filtrate and washings were evaporated to dryness in vacuo. The residual oil, containing the crude 3-O-formyl-16-deacetoxy-16β-(2'-fluoroethoxy)fusidic acid benzoyloxymethyl ester, was dissolved in methanol (85 ml), potassium carbonate (3.46 g; 25 mmol) was added, and the mixture was stirred at room temperature for 30 minutes. The major part of the solvent was removed by evaporation in vacuo, and to the residue was added water (100 ml) and ether (100 ml). After acidification of the stirred mixture with 4 N hydrochloric acid, the organic layer was separated, the aqueous layer reextracted with ether (50 ml), and the combined organic phases were washed with water until neutral. In order to separate the desired acid derivatives from 16-deacetylfusidic acid lactone, being formed as a by-product, the ethereal solution obtained above was extracted with 0.5 N sodium hydroxide (3 × 50 ml) and washed with water (3 × 25 ml). To the combined aqueous phases and washings was added ether (100 ml), and the stirred mixture was acidified with 4 N hydrochloric acid. After separation of the organic layer, the aqueous layer was extracted with ether (50 ml), and the combined organic extracts were washed with water until neutral, dried, and evaporated in vacuo. The resulting amorphous residue was dissolved in diisopropyl ether (30 ml), and on scratching a crystalline product precipitated. After being kept in the refrigerator overnight, the crystals were filtered off, washed with diisopropyl ether, and dried to afford 2.32 g of 16-deacetoxy-16β-(2'-fluoroethoxy)fusidic acid, melting point: 158°-160° C. From the mother liquor a further 0.48 g of the desired compound, melting point: 155°-159° C, was obtained. Two recrystallizations from methanol-diisopropyl ether gave the analytically pure product, melting point: 162°-163° C.

EXAMPLES 51-52

16-Deacetoxy-16β-alkyloxyfusidic acids

Following the procedure of Example 50, but substituting the alcohols listed in table XIV for the 2-fluoroethanol, the 16-deacetoxy-16β-alkyloxyfusidic acids indicated in table XIV were obtained.

Table XIV

| Example | Alcohol | Resulting compound R | Mp (° C) |
|---|---|---|---|
| 51 | 2-Acetoxyethanol | $CH_2CH_2OH$ | 179–182 |
| 52 | 1,3-Difluoropropanol-(2) | $CH(CH_2F)_2$ | 169–171 |

EXAMPLES 53-62

16β-Ethers of 16-deacetoxyfusidic acid

Following the procedure of Example 50, but substituting 16-deacetoxy-16α-bromofusidic acid acetoxymethyl ester for the 3-O-formyl-16-deacetoxy-16α-bromofusidic acid benzoyloxymethyl ester and the alcohols listed in table XV for the 2-fluoroethanol, the 16β-ethers of 16-deacetoxyfusidic acid indicated in table XV were obtained.

Table XV

| Example | Alcohol | Resulting compound R | Mp (° C) |
|---|---|---|---|
| 53 | Isopropanol | $CH(CH_3)_2$ | 189–190 |
| 54 | tert.Butanol | $C(CH_3)_3$ | 179–180 |
| 55 | 2,2-Dichloroethanol | $CH_2CHCl_2$ | 181–182 |
| 56 | 2,2,2-Trichloroethanol | $CH_2CCl_3$ | 212–213 |
| 57 | 1,3-Difluoropropanol-(2) | $CH(CH_2F)_2$ | 169–171 |
| 58 | 1,3-Diacetoxypropanol-(2) | $CH(CH_2OH)_2$ | amorphous |
| 59 | Allyl alcohol | $CH_2CH=CH_2$ | 154–156 |
| 60 | 2-Butenol-(1) | $CH_2CH=CHCH_3$ | 128–135(dec.) |
| 61 | 2-Propynol-(1) | $CH_2C\equiv CH$ | 134–136 |
| 62 | Cyclopentanol | cyclopentyl | 188–189 |

EXAMPLE 63

16-Deacetoxy-16β-ethoxy-24,25-dihydrofusidic acid

A. 3-O-Acetyl-16-epideacetyl-24,25-dihydrofusidic acid pivaloyloxymethyl ester To a solution of 3-O-acetyl-16-epideacetyl-24,25-dihydrofusidic acid (31.12 g; 60 mmol) in dimethylformamide (250 ml) was added triethylamine (11.92 ml; 84 mmol) and, after stirring for 15 minutes, chloromethyl pivalate (17.76 ml; 120 mmol). After stirring for 20 hours at room temperature, the mixture was diluted with ethyl acetate (750 ml) and washed thoroughly with water (4 × 250 ml, 2 × 50 ml) to remove unreacted starting material and the greater part of dimethylformamide. The organic phase was dried and evaporated in vacuo to yield 42 g of an oily residue. The residue was dissolved in ether (50 ml), petroleum ether (200 ml) was added, and the mixture was stirred for two hours. The crystalline precipitate thus obtained was filtered off, washed with ether:petroleum ether 1:4. The combined filtrate and washings were evaporated to dryness in vacuo to give 36 g of crude 3-O-acetyl-16-epideacetyl-24,25-dihydrofusidic acid pivaloyloxymethyl ester as a foam which failed to crystallize.

B. 3-O-Acetyl-16-deacetoxy-16α-methanesulfonyloxy-24,25-dihydrofusidic acid pivaloyloxymethyl ester To a stirred solution of crude 3-O-acetyl-16-epideacetyl-24,25-dihydrofusidic acid pivaloyloxymethyl ester (30 g; containing ∼ 45 mmol of pure compound) in a mixture of methylene chloride (75 ml) and pyridine (75 ml) was added dropwise at −20° C a solution of methanesulfonyl chloride (13.8 ml; ∼ 180 mmol) in methylene chloride (25 ml). After the addition was finished (ca. 15 minutes), the mixture was stirred at −15° C for 1.5 hours and then kept in the refrigerator overnight. Ice (ca. 15 g) was added and, after stirring for 0.5 hour, the mixture was poured into a mixture of ether (250 ml) and water (100 ml) and shaken vigorously. The organic layer was separated and the aqueous phase reextracted with ether (100 ml). The combined organic phases were washed with water, 4 N hydrochloric acid (to remove pyridine), saturated aqueous sodium chloride, 0.5 M aqueous sodium bicarbonate, and once more saturated aqueous sodium chloride, dried, and evaporated in vacuo to yield 28.5 g og crude 3-O-acetyl-16-deacetoxy-16α-methanesulfonyloxy-24,25-dihydrofusidic acid pivaloyloxymethyl ester as a yellowish foam which failed to crystallize. The relatively unstable product was used for the next step without further purification; IR (KBr): 1170 and 1365 cm⁻¹.

C.

3-O-Acetyl-16-deacetoxy-16β-ethoxy-24,25-dihydrofusidic acid pivaloyloxymethyl ester A solution of crude 3-O-acetyl-16-deacetoxy-16α-methanesulfonyloxy-24,25-dihydrofusidic acid pivaloyloxymethyl ester (2.6 g) in ethanol (25 ml) was stirred at 60°-65° C for 2 hours. Water (100 ml) was added, and the mixture was extracted with ethyl acetate (2 × 25 ml). The combined organic extracts were washed with water, dried, and evaporated in vacuo to give 1.98 g of a yellowish gum. The residue was purified by dry column chromatography on silica gel (cyclohexane ethyl acetate 85:15) to yield 0.72 g of 3-O-acetyl-16-deacetoxy-16β-ethoxy-24,25-dihydrofusidic acid pivaloyloxymethyl ester as a colourless foam.

D. 16-Deacetoxy-16β-ethoxy-24,25-dihydrofusidic acid

To a solution of the 16β-ethoxy ester described above in ethanol (10 ml) was added 5 N aqueous sodium hydroxide (2 ml), and the mixture was kept at room temperature overnight. After addition of water (50 ml), the mixture was acidified with 4 N hydrochloric acid and extracted with ethyl acetate (2 × 25 ml). The combined organic extracts were washed with water, dried, and evaporated in vacuo to leave 0.52 g of an amorphous product which crystallized from ether. The crystals were filtered off, washed with ether and dried to afford 0.26 g of 16-deacetoxy-16β-ethoxy-24,25-dihydrofusidic acid, melting point: 189°-191° C. Two recrystallizations from ether gave the analytical sample, melting point: 192°-193° C.

EXAMPLE 64

16-Deacetoxy-16β-methoxy-24,25-dihydrofusidic acid

A.

3-O-Acetyl-16-deacetoxy-16β-methoxy-24,25-dihydrofusidic acid pivaloyloxymethyl ester Following the procedure for Example 63 A–C, but substituting methanol for the ethanol, 3-O-acetyl-16-deacetoxy-16β-methoxy-24,25-dihydrofusidic acid pivaloyloxymethyl ester was obtained.

B. 16-Deacetoxy-16β-methoxy-24,25-dihydrofusidic acid

By substituting 3-O-acetyl-16-deacetoxy-16β-methoxy-24,25-dihydrofusidic acid pivaloyloxymethyl ester for the corresponding 16β-ethoxy derivative in the procedure of Example 63 D, 16-deacetoxy-16β-methoxy-24,25-dihydrofusidic acid, melting point 152°-154° C, was obtained.

EXAMPLE 65

16-Deacetoxy-16β-propyloxyfusidic acid

A.

3-O-Acetyl-16-deacetoxy-16α-methanesulfonyloxyfusidic acid pivaloyloxymethyl ester A solution of methanesulfonyl chloride (4.6 ml; ~60 mmol) in methylene chloride (10 ml) was added dropwise at −20° C to a stirred solution of crude 3-O-acetyl-16-epideacetylfusidic acid pivaloyloxymethyl ester (10 g; containing ~15 mmol of pure compound) in a mixture of methylene chloride (25 ml) and pyridine (25 ml), placed in a 3-necked 250 ml-flask equipped with a thermometer, a dropping funnel, and a drying tube. After the addition was finished, the mixture was stirred at −15° C for 1.5 hours and then kept in the refrigerator overnight. Ice (ca. 5 g) was added, and after stirring for 0.5 hour, the mixture was poured into water (50 ml) and extracted with ether (2 × 50 ml). The combined organic phases were washed with water, 4 N hydrochloric acid (to remove pyridine), saturated aqueous sodium chloride, 0.5 M aqueous sodium bicarbonate, and again saturated aqueous sodium chloride, dried, and evaporated in vacuo to afford 10.6 g of crude 3-O-acetyl-16-deacetoxy-16α-methanesulfonyloxyfusidic acid pivaloyl-oxymethyl ester as a yellowish amorphous product. The unstable compound was used for the next step without further purification.

IR (KBr): 1170 and 1355 cm⁻¹.

By using the method described above, but substituting p-toluenesulfonyl chloride for the methanesulfonyl chloride, the corresponding 16α-p-toluenesulfonyloxy derivative was prepared.

B. 16-Deacetoxy-16β-propyloxyfusidic acid

To a solution of crude 3-O-acetyl-16-deacetoxy-16α-methanesulfonyloxyfusidic acid pivaloyloxymethyl ester (1.42 g; ~2 mmol) in propanol-(1) (10 ml) was added triethylamine (0.28 ml; 2 mmol), and the mixture was stirred at room temperature for 42 hours. After dilution with ethyl acetate (40 ml), the mixture was washed with water, diluted hydrochloric acid, and water, dried, and evaporated in vacuo to give 1.28 g of an amorphous product. This residue was purified by dry column chromatography on silica gel (petroleum ether: ethyl acetate; 85:15) to yield 0.36 g of 3-O-acetyl-16-deacetoxy-16β-propyloxyfusidic acid pivaloyloxymethyl ester as a colourless foam. The above ester was hydrolyzed by refluxing its solution in ethanol (5 ml) with 5 N aqueous sodium hydroxide (1 ml) for 2 hours. After a similar work-up procedure as described in Example 63 D, crystalline 16-deacetoxy-16β-propyloxyfusidic acid, melting point: 176°-177° C, was obtained.

EXAMPLES 66–70

16-Deacetoxy-16β-alkyloxyfusidic acids

By substituting the alcohols listed in table XVI for the propanol-(1) in the procedure of Example 65, the 16-deacetoxy-16β-alkyloxyfusidic acids indicated in table XVI were obtained.

Table XVI

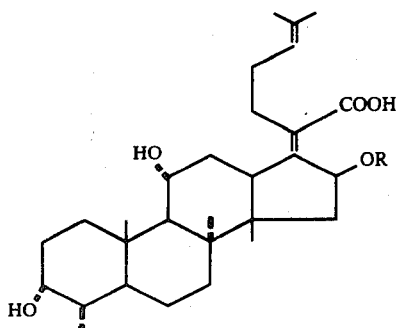

| Example | Alcohol | Resulting compound R | Mp (° C) |
|---|---|---|---|
| 66 | Butanol-(1) | $CH_2CH_2CH_2CH_3$ | 167–169 |
| 67 | iso-Butanol | $CH_2CH(CH_3)_2$ | 189–190 |
| 68 | 2-Methoxyethanol | $CH_2CH_2OCH_3$ | 163–165 |
| 69 | 2-Chloroethanol | $CH_2CH_2Cl$ | 158–159 |
| 70 | Benzylalcohol | $CH_2C_6H_5$ | 113–119 |

EXAMPLE 71

16-Deacetoxy-16β-(2'-azidoethoxy)fusidic acid

A.
3-O-Acetyl-16-deacetoxy-16β-(2'-hydroxyethyloxy)-fusidic acid phenacyl ester

To a solution of 3-O-acetyl-16-deacetoxy-16α-bromofusidic acid phenacyl ester (13.96 g; 20 mmol) in a 1:1 mixture of ethylene glycol mono- and diacetate (80 ml) was added silver carbonate (11.03 g; 40 mmol). After being protected from light, the mixture was stirred for 3 days at room temperature. Insoluble material was filtered off and washed with ether (2 × 20 ml). After removal of the solvent from the combined filtrate and washings at reduced pressure, the liquid residue was diluted with methanol (320 ml), potassium carbonate (5.53 g; 40 mmol) was added, and the mixture was stirred for 30 minutes at room temperature. The mixture was evaporated in vacuo, and the oily residue thus obtained was dissolved in a mixture of ether (200 ml) and water (200 ml). After acidification of the stirred mixture with diluted hydrochloric acid, the organic phase was separated and the aqueous phase reextracted with ether (100 ml). The combined organic extracts were washed with water until neutral, dried, and evaporated in vacuo. The yellowish amorphous residue thus obtained was purified by dry column chromatography on silicagel (petroleum ether — ethyl acetate; 6:4) to give 5.54 g of the desired compound as a colourless amorphous powder which failed to crystallize.

B.
3-O-Acetyl-16-deacetoxy-16β-(2'-bromoethoxy)fusidic acid phenacyl ester

Phenyl N,N-dimethylformimidate bromide (4.6 g; ~20 mmol) was added to a solution of 3-O-acetyl-16-deacetoxy-16β-(2'-hydroxyethyloxy)fusidic acid phenacyl ester (4.21 g; 6.2 mmol) in dimethylformamide (25 ml), and the mixture was stirred for 16 hours at room temperature. After dilution with ether (100 ml), the mixture was washed with water (4 × 25 ml), and the remaining organic phase was dried and evaporated in vacuo. The oily residue thus obtained was purified by dry column chromatography on silicagel (petroleum ether—ethyl acetate; 85:15) to give 3.16 g of 3-O-acetyl--16-deacetoxy-16β-(2'-bromoethoxy)fusidic acid phenacyl ester as a colourless amorphous product.

3-O-Acetyl-16-deacetoxy-16β-(2'-azidoethoxy)fusidic acid phenacyl ester

A solution of 3-O-acetyl-16-deacetoxy-16β-(2'-bromoethoxy)fusidic acid phenacyl ester (1.04 g; 1.4 mmol) and lithium azide (0.34 g; 7 mmol) in dimethylformamide (20 ml) was stirred for 16 hours at room temperature. The mixture was diluted with ether (80 ml), washed with water (4 × 20 ml), and the organic phase was dried and evaporated in vacuo to yield 0.97 g of the desired compound as a foam. IR (KBr): 2100 cm$^{-1}$(—N$_3$).

D. 16-Deacetoxy-16β-(2'-azidoethoxy)fusidic acid

To a solution of 3-O-acetyl-16-deacetoxy-16β-(2'-azidoethoxy)fusidic acid phenacyl ester (0.95 g; 1.34 mmol) in ethanol (20 ml) was added 5 N aqueous sodium hydroxide (2.7 ml), and the mixture was stirred for 18 hours at room temperature. The solvent was removed in vacuo, and the resulting oily residue was dissolved in water (40 ml) and extracted with ether (20 ml). The aqueous phase was separated, acidified with diluted hydrochloric acid, and the oily precipitate which formed was twice extracted with ether. The combined ethereal extracts were washed with water, dried, and evaporated to give 0.8 g of an amorphous product which crystallized from diisopropyl ether to yield 0.41 g of 16-deacetoxy-16β(2'-azidoethoxy)fusidic acid, mp. 179°–182° C. Two recrystallizations from the same solvent gave the analytically pure compound, melting point 184°–185° C.

EXAMPLE 72

16-Deacetoxy-16β-ethoxy-24,25-dihydrofusidic acid

A. 16-Deacetoxy-16β-ethoxyfusidic acid benzyl ester

To a solution of 16-deacetoxy-16α-bromofusidic acid benzyl ester (3.14 g; 5 mmol) in ethanol (25 ml) was added silver carbonate (2.76 g; 10 mmol), and, after protection from light, the mixture was stirred at room temperature for 16 hours. The insoluble material was filtered off, washed with ethanol (2 × 5 ml), and the combined filtrate and washings were evaporated in vacuo. The amorphous residue thus obtained was purified by dry column chromatography on silica gel (petroleum ether: ethyl acetate; 60:40) to yield 1.66 g of the desired compound as a colourless foam.

B. 16-Deacetoxy-16β-ethoxy-24,25-dihydrofusidic acid

10% Palladium on carbon catalyst (0.4 g ) was added to a solution of 16-deacetoxy-16β-ethoxyfusidic acid benzyl ester (1.2 g; ~2 mmol) in ethanol (20 ml), and the mixture was shaken in a hydrogen atmosphere for 40 minutes. The catalyst was filtered off, washed with ethanol, and the combined filtrate and washings were evaporated in vacuo. The resulting residue was crystallized from ether to afford 0.92 g of 16-deacetoxy-16β-ethoxy-24,25-dihydrofusidic acid, melting point: 191°–192° C.

EXAMPLE 73

16-Deacetoxy-16β-(2',2',2'-trifluoroethoxy)-24,25-dihydrofusidic acid

To a solution of 16-deacetoxy-16β-(2',2',2'-trifluoroethoxy)fusidic acid (278 mg; 0.5 mmol) in 96% ethanol (5 ml) was added 10% palladium on calcium carbonate catalyst (50 mg), and the mixture was shaken in a hydrogen atmosphere for 20 minutes. The catalyst was filtered off, washed with 96% ethanol, and the combined filtrate and washings were evaporated to dryness in vacuo. The residue crystallized from diisopropyl ether to afford 220 mg of the desired compound, melting point: 204°–205° C. Recrystallization from the same solvent gave the analytical sample, melting point: 204°–205° C.

EXAMPLE 74

16-Deacetoxy-16β-(2'-fluoroethoxy-)-24,25-dihydrofusidic acid

By substituting 16-deacetoxy-16β-(2'-fluoroethoxy) fusidic acid for the 16-deacetoxy-16β-(2',2',2'-trifluoroethoxy)fusidic acid in the procedure of Example 73 16-deacetoxy-16β-(2'-fluoroethoxy)-24,25-dihydrofusidic acid, melting point: 180°–182° C was obtained.

EXAMPLE 75

11-Keto-16-deacetoxy-16β-ethoxyfusidic acid

To a suspension of 3-O-acetyl-11-keto-16-deacetoxy-16α-bromofusidic acid phenacyl ester (5.57 g; 8 mmol) in ethanol (60 ml) was added silver carbonate (4.41 g; 16 mmol), and, after being protected from light, the mixture was stirred for 18 hours at room temperature. Insoluble material was filtered off and washed with ethanol (2 × 20 ml). The combined filtrate and washings containing the crude 3-O-acetyl-11-keto-16-deacetoxy-16β-ethoxyfusidic acid phenacyl ester were diluted with ethanol (80 ml), 5 N aqueous sodium hydroxide (32 ml) was added, and the mixture was stirred for 20 hours at room temperature. The solvent was removed in vacuo, to the residual oil was added water (100 ml) and ether (100 ml), and the stirred mixture was acidified by addition of 4 N hydrochloric acid. The organic phase was separated, the aqueous phase was reextracted with ether (100 ml), and the combined organic extracts were washed with water until neutral, dried, and evaporated in vacuo. The resulting oily residue was purified by dry column chromatography on silicagel (ether : petroleum ether : acetic acid, 50:50:0.5), and the yellowish amorphous product thus obtained crystallized from diisopropyl ether to give 2.12 g of 11-keto-16-deacetoxy-16β-ethoxyfusidic acid, melting point 166°–167° C. Recrystallization from etherdiisopropyl ether afforded the analytical sample, melting point 167°–168° C.

EXAMPLE 76

11-Keto-16-deacetoxy-16β-(2'-fluoroethoxy)fusidic acid

Following the procedure described in Example 75 but substituting 2-fluoroethanol for the ethanol, 11-keto-16-deacetoxy-16β-(2'-fluoroethoxy)fusidic acid was obtained as a colourless, amorphous powder. The compound could be converted into a crystalline sodium salt (see Example 88).

EXAMPLE 77

3,11-Diketo-16-deacetoxy-16β-ethoxyfusidic acid

Jones' reagent (12.0 ml) was added dropwise at 15° C to a stirred solution of 16-deacetoxy-16β-ethoxyfusidic acid (10.24 g of the hemihydrate; 20 mmol) in acetone (200 ml). After the addition was finished, the cooling-bath was removed, and the mixture was stirred for 30 minutes at room temperature. To the mixture was added ether (300 ml) and water (200 ml), and stirring was continued for 15 minutes. The organic layer was separated, the aqueous phase was reextracted with ether (100 ml), and the combined organic extracts were washed with water until neutral, and dried. On concentration of the ethereal solution to about 100 ml, crystallization of a colourless product began. After being kept in the refrigerator overnight, the crystals were collected, washed with ether, and dried to afford 7.02 g of 3,11-diketo-16-deacetoxy-16β-ethoxyfusidic acid, melting point 185°–187° C. Concentration of the mother liquor gave another 0.84 g of the desired compound. The analytical sample, melting point 187°–188° C, was obtained on recrystallization from methylene chloride-diisopropyl ether.

EXAMPLE 78

3-Keto-16-deacetoxy-16β-ethoxyfusidic acid

A mixture of 3,11-diketo-16-deacetoxy-16β-ethoxyfusidic acid (6.05 g; 12.14 mmol), 2ethyl-2-methyl dioxolane(-1,3) (60 ml), and p-toluenesulfonic acid (0.24 g) was refluxed for 40 minutes on an electric heating-bath. After cooling to room temperature, ether (200 ml) and pyridine (0.5 ml) were added, and the mixture was washed with water (4 x 50 ml). The organic phase was dried and evaporated in vacuo to leave 7.06 g of the crude 3-ethylene ketal of the 3,11-diketo acid as a gum, which failed to crystallize.

To a stirred solution of the above residue in ethanol (140 ml) was added at 5° C solid sodium borohydride (2 g) in portions. After the addition was finished, the cooling-bath was removed, and the mixture was stirred for 45 minutes at room temperature. The mixture was neutralized with acetic acid, water (420 ml) was added, and the oily precipitate which formed was extracted with ether (2 × 150 ml). The combined organic extracts were washed with water (4 × 25 ml), dried, and evaporated in vacuo. The resulting oily residue was crystallized from ether-diisopropyl ether to afford 3.12 g of the 3-ethylene ketal of 3-keto-16-deacetoxy-16β-ethoxyfusidic acid, melting point 166°–169° C. Concentration of the mother liquor furnished another 2.04 g of the desired compound, melting point 166°–169° C. Two recrystallizations from methylene chloride-dissopropyl ether gave the analytical sample, melting point 171°–172° C.

A solution of 3-keto-16-deacetoxy-16β-ethoxyfusidic acid 3-ethylene ketal (3.98 g; 7.3 mmol) in methanol (40 ml) was acidified with 2 N hydrochloric acid (2 ml) and refluxed for 20 minutes on the steam-bath. After cooling, water (160ml) was added, and the oily precipitate, which formed, was extracted with ether (2 × 100 ml). The combined organic extracts were washed with water until neutral, dried, and evaporated in vacuo. The resulting amorphous residue was crystallized from ether to yield 2.94 g of 3-keto-16-deacetoxy-16β-ethoxyfusidic acid, melting point 175°–177 °C. Recrystallization from the same solvent raised the melting point to 177°–179° C.

EXAMPLE 79

16-Deacetoxy-16β-isopropylsulfinylfusidic acid

β-diethylaminoethyl ester

To a solution of the sodium salt of 16-deacetoxy-16β-isopropylsulfinylfusidic acid (320 mg; 0.5 mmol) in 2 ml of dimethylformamide was added β-(diethylamino)ethyl chloride (0.08 ml; 0.55 mmol). A crystalline product started to precipitate when this mixture was left at room temperature for 5 hours. Water (5 ml) was then added, and the product was filtered off, washed with 5 ml of water and dried to afford 310 mg of 16-deacetoxy-16β-isopropylsulfinylfusidic acid β-diethylaminoethyl ester, melting point 156°-158° C.

EXAMPLE 80

16-Deacetoxy-16β-isopropylsufinylfusidic acid acetoxymethyl ester

To a solution of the sodium salt of 16-deacetoxy-16β-isopropylsulfinylfusidic acid (320 mg; 0.5 mmol) in 2 ml of dimethylformamide was added chloromethyl acetate (0.05 ml; 0.55 mmol). After standing for 124 hours at room temperature, ethanol (5 ml) and water (5 ml) was added to precipitate the desired product as colourless crystals, which were filtered off, washed with water (5 ml), and dried to give 290 mg; melting point 151°-153° C. Recrystallization from ethyl acetatepetroleum ether raised the melting point to 152-154° C.

EXAMPLE 81

16-Deacetoxy-16β-isopropylthiofusidic acid acetoxymethyl ester

By following the procedure described in Example 80 and substituting 16-deacetoxy-16β-isopropylthiofusidic acid for 16-deacetoxy-16β-isopropylsulfinylfusidic acid 16-deacetoxy-16β-isopropylthiofusidic acid acetoxymethyl ester was prepared as colourless crystals of melting point 77°-83° C.

EXAMPLES 82-89

Sodium salts of 16β-ethers, 16β-thioethers and 16β-alkylsulphinyl compounds of 16-deacetoxylfusidic acid and its 3- and 11-keto derivatives.

Crystalline sodium salts of the compounds described in Examples 1, 35, 46, 48, 50, 75, 76, and 78 were obtained by the following procedure: A solution of the corresponding acid (10 mmol) in methanol (25 ml) was titrated with 2 N methanolic sodium hydroxide using phenolphthalein as an indicator. After evaporation to dryness in vacuo, the oily or amorphous residue thus obtained was taken up in acetone (ca. 100 ml), the resulting solution was concentrated to about half the volume, and upon scratching the desired sodium salt began to crystallize. The mixture was kept for 2 hours at room temperature, thereafter the crystals were collected, washed with acetone, and dried to give the pure sodium salt of the desired compound.

The sodium salts prepared by this method are listed in table XVII. Microanalysis, IR-and NMR data obtained for these compounds are in agreement with their structure.

Table XVII

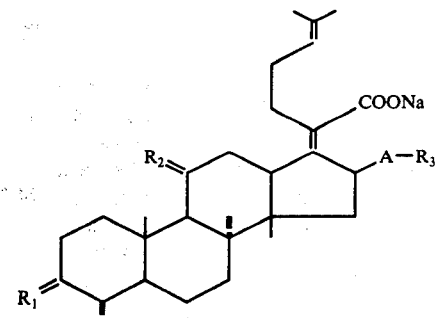

| Ex. | $R_1$ | $R_2$ | A | $R_3$ | Acid described in Example |
|---|---|---|---|---|---|
| 82 | H,α—OH | H,α—OH | S | $CH(CH_3)_2$ | 1 |
| 83 | H,α—OH | H,α—OH | S → O | $CH(CH_3)_2$ | 35 |
| 84 | H,α—OH | H,α—OH | O | $CH_2CH_3$ | 46 |
| 85 | H,α—OH | H,α—OH | O | $CH_2CF_3$ | 48 |
| 86 | H,α—OH | H,α—OH | O | $CH_2CH_2F$ | 50 |
| 87 | H,α—OH | O | O | $CH_2CH_3$ | 75 |
| 88 | H,α—OH | O | O | $CH_2CH_2F$ | 76 |
| 89 | O | H,α—OH | O | $CH_2CH_3$ | 78 |

EXAMPLE 90

Potassium salt of 16-deacetoxy-16β-(2'-hydroxyethoxy)fusidic acid

A solution of 16-deacetoxy-16β-(2'-hydroxyethoxy)-fusidic acid (2.64 g; 5 mmol, calculated as the hemihydrate) in methanol (10 ml) was titrated against phenolphthalein with 2 N methanolic potassium hydroxide. After evaporation to dryness in vacuo, the amorphous residue thus obtained was dissolved in methanol (2.5 ml), acetone (60 ml) was added, and the mixture was concentrated to about 15 ml of reduced pressure. Colourless crystals precipitated on scratching, were filtered off, washed with acetone, and dried to afford 2.32 g of the desired compound.

EXAMPLE 91

16-Deacetoxy-3-keto-16β-isopropylthio-24,25-dihydrofusidic acid

By following the procedure of Example 34 and substituting 16-deacetoxy-16β-isopropylthio-24,25-dihydrofusidic acid acetoxymethyl ester for 16-deacetoxy-16β-isopropylthiofusidic acid acetoxymethyl ester, 16-deacetoxy-3-keto-16β-isopropylthio-24,25-dihydrofusidic acid was prepared.

EXAMPLE 92

11-Keto-16-deacetoxy-16β-(2',2',2'-trifluoroethoxy) fusidic acid

Following the procedure described in Example 75 but substituting 2,2,2-trifluoroethanol for the ethanol, 11-keto-16-deacetoxy-16β-(2',2',2'-trifluoroethoxy)fusidic acid was obtained.

Example 93

| Cream | |
|---|---|
| 16-Deacetoxy-16β-isopropylthio-24,25-dihydrofusidic acid | 20 g |
| Petrolatum | 150 g |
| Liquid paraffin | 150 g |
| Spermaceti | 50 g |
| Sorbitan monopalmitate | 50 g |
| Polyoxyethylene sorbitan monopalmitate | 50 g |
| Water | 530 g |

Example 93-continued

| Cream | |
|---|---|
| | 1000 g |

Heat petrolatum, paraffin, spermaceti, sorbitan-monopalmitate, and polyoxyethylene sorbitan monopalmitate to 70° C and add slowly the water at 72° C with agitation. Continue agitation until the cream has cooled. Triturate 16-deacetoxy-16β-isopropylthio-24,25-dihydrofusidic acid into the cream base and homogenize using a roller mill. Fill the cream into laquered aluminum collapsible tubes.

Example 94

| Ointment | |
|---|---|
| 16-Deacetoxy-16β-isopropylthiofusidic acid sodium salt | 20 g |
| Liquid paraffin | 138 g |
| Cetanol | 4 g |
| Lanolin anhydrous | 46 g |
| Petrolatum | 792 g |
| | 1000 g |

Melt paraffin, cetanol, lanolin, and petrolatum at 70° C. After cooling to below 40° C, triturate 16-deacetoxy-16β-isopropylthiofusidic acid sodium salt. Fill the ointment into lacquered collapsible aluminum tubes.

Example 95

| Ointment | |
|---|---|
| 16-Deacetoxy-16β-isopropylsulphinyl fusidic acid sodium salt | 10 g |
| Liquid paraffin | 138 g |
| Centanol | 4 g |
| Lanolin anhydrous | 46 g |
| Petrolatum | 802 g |
| | 1000 g |

Melt paraffin, cetanol, lanolin, and petrolatum at 70° C. After cooling to below 40° C, triturate 16-deacetoxy-16β-isopropylsulphinyl fusidic acid sodium salt. Fill the ointment into laquered collapsible tubes.

Example 96

| Capsule | |
|---|---|
| 11-Keto-16-deacetoxy-16β-ethoxyfusidic acid sodium salt | 250 g |
| Microcrystalline cellulose | 145 g |
| Magnesium stearate | 5 g |
| | 400 g |

Pass the ingredients through a 60 mesh sieve and mix for 10 minutes. Fill the mixture into hard gelatin capsules No. 00 (Parke Davis & Co.) using a capsule fil weight of 400 mg.

Example 97

| Preparation of tablets | |
|---|---|
| 16-Deacetoxy-16β-(2',2',2'-trifluoro-ethoxy)fusidic acid | 250 g |
| Avicel PH 101 | 120 g |
| STA-Rx 1500 | 120 g |
| Magnesiumstearate | 10 g | p 16-Deacetoxy-16β-(2',2',2'-trifluoroethoxy)fusidic acid, Avicel and STA-Rx are mixed together, sieved through a 0.7 mm sieve and thereafter mixed with the magnesiumstearate. The mixture is pressed into tablets each of 500 mg.

Example 98

| Preparation of suspension | |
|---|---|
| 3-Keto-16-deacetoxy-16β-isopropylthio-fusidic acid | 5.00 g |
| Citric acid | 0.45 g |

Example 98-continued

| Preparation of suspension | |
|---|---|
| Sodium monohydrogenphosphate | 0.70 g |
| Sucrose | 25.00 g |
| Tween 80 | 0.05 g |
| Potassium sorbate | 0.20 g |
| Carboxymethylcellulose-Na | 0.50 g |
| Purified water | qs to 100 ml suspension |

The crystals are micronized and suspended in a solution of the citric acid, the sodium monohydrogenphosphate, the sucrose, the potassium sorbate and the Tween 80 in 50 ml water, if necessary under slight warming. The carboxymethylcellulose-Na is dissolved in 20 ml of boiling water. After cooling, it is added to the other ingredients. The suspension is homogenized in a blender and finally purified water is added to a total volume of 100 ml.

Example 99

| Ointment | |
|---|---|
| A: 16-Deacetoxy-16β-isopropylthio-fusidic acid sodium salt | 20 g |
| B: One of the steroids: hydrocortison, triamcinolon or fluocinolon | 10 g |
| Liquid paraffin | 138 g |
| Cetanol | 4 g |
| Lanolin anhydrous | 46 g |
| Petrolatum | 802 g |
| | 1000 g |

Melt paraffin, cetanol, lanolin, and petrolatum at 70° C. After cooling to below 40° C, triturate A and B. Fill the ointment into laquered collapsible tubes.

Example 100

| A: 16-Deacetoxy-16β-(2'-fluoroethoxy) fusidic acid | 125 g |
|---|---|
| B: One of the antibiotics: Amoxycillin, Cephalexin, Rifamycin, Rifampicin, Clindamycin or Lincomycin, Erythromycin, Pivmecillinam | 125 g |
| Microcrystalline cellulose | 145 g |
| Magnesium stearate | 5 g |
| | 400 g |

Pass the ingredients through a 60 mesh sieve and mix for 10 minutes. Fill the mixture into hard gelatin capsules No. 00 (Parke Davis & Co.) using a capsule fil weight of 400 mg.

Example 101

| Ointment | |
|---|---|
| A: Tetracycline | 15 g |
| B: 15-Deacetoxy-16β-ethoxyfusidic acid | 15 g |
| Liquid paraffin | 138 g |
| Cetanol | 4 g |
| Lanolin anhydrous | 46 g |
| Petrolatum | 782 g |

Melt paraffin, cetanol, lanolin, and petrolatum at 70° C. After cooling to below 40° C, triturate A and B. Fill the ointment into laquered collapsible aluminium tubes.

What we claim is:

1. A compound of the following formula I:

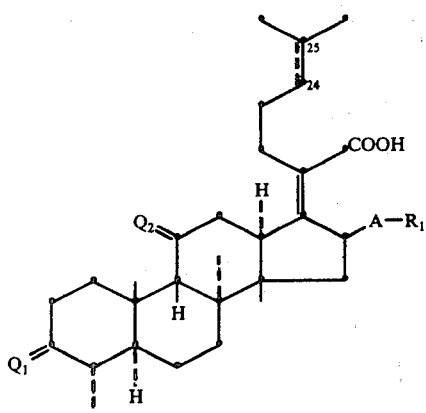

in which the $C_{24-25}$ bond is a single or a double bond, and in which $Q_1$ and $Q_2$ stand for

or oxygen; A stands for oxygen, sulphur or a sulfinyl radical; $R_1$ stands for a straight or branched alkyl radical having from 1 to 8 carbon atoms, an alkenyl or alkynyl radical having from 2 to 6 carbon atoms, a cycloalkyl radical having from 3 to 7 carbon atoms in the alkyclic ring, an aryl, aralkyl or heterocyclylalkyl radical, or a heterocyclic radical having 5 or 6 ring atoms and containing oxygen, sulphur or nitrogen selected from the group consisting of 2- or 3-pyrrolyl, 2- or 3-furyl, 2- or 3-thienyl, 2-, 3- or 4-pyridyl, 2-, 4- or 5-pyrimidinyl, 2- or 3-pyrazolyl, imidazolyl, triazolyl, tetrazolyl, thiazolyl and thiadiazolyl, all $R_1$ radicals being optionally substituted; and non-toxic pharmaceutically acceptable salts and easily hydrolyzable esters thereof.

2. A compound of formula I, in which the $C_{24-25}$ bond is a single or a double bond, $Q_1$ and $Q_2$ both stand for

A stands for oxygen; $R_1$ stands for a straight or branched alkyl radical having from 1 to 4 carbon atoms and being optionally substituted with halogen atoms, hydroxy or azido groups, and non-toxic pharmaceutically acceptable salts and easily hydrolyzable esters thereof.

3. A compound of formula I, in which the $C_{24-25}$ bond is a single or a double bond, $Q_1$ and $Q_2$ both stand for

A stands for sulphur; $R_1$ stands for a straight or branched alkyl radical having from 1 to 4 carbon atoms and being optionally substituted with halogen atoms, hydroxy or azido groups, and non-toxic pharmaceutically acceptable salts and easily hydrolyzable esters thereof.

4. A compound of formula I, in which the $C_{24-25}$ bond is a single or a double bond, $Q_1$ and $Q_2$ both stand for

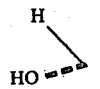

A stands for a sulfinyl radical; $R_1$ stands for a straight or branched alkyl radical having from 1 to 4 carbon atoms and being optionally substituted with halogen atoms, hydroxy or azido groups, and pharmaceutically acceptable salts and non toxic easily hydrolyzable esters thereof.

5. A compound of formula I, in which the $C_{24-25}$ bond is a single or a double bond, one of $Q_1$ and $Q_2$ is oxygen and the other is

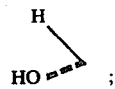

A stands for oxygen; $R_1$ stands for a straight or branched alkyl radical having from 1 to 4 carbon atoms and being optionally substituted with halogen atoms, hydroxy or azido groups, and non-toxic pharmaceutically acceptable salts and easily hydrolyzable esters thereof.

6. A compound of formula I, in which the $C_{24-25}$ bond is a single or a double bond, one of $Q_1$ and $Q_2$ is oxygen and the other is

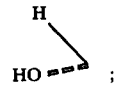

A stands for sulphur; $R_1$ stands for a straight or branched alkyl radical having from 1 to 4 carbon atoms and being optionally substituted with halogen atoms, hydroxy or azido groups, and non-toxic pharmaceutically acceptable salts and easily hydrolyzable esters thereof.

7. A compound of formula I, in which the $C_{24-25}$ bond is a single or a double bond, one of $Q_1$ and $Q_2$ is oxygen and the other is $$\begin{array}{c} H \\ \diagdown \\ HO \cdots \diagup \end{array} ;$$

A stands for sulfinyl; $R_1$ stands for a straight or branched alkyl radical having from 1 to 4 carbon atoms and being optionally substituted with halogen atoms, hydroxy or azido groups, and non-toxic pharmaceutically acceptable salts and easily hydrolyzable esters thereof.

8. 16-Deacetoxy-16β-isopropylthiofusidic acid and its $C_{24-25}$-dihydro analogue and non-toxic pharmaceutically acceptable salts and easily hydrolyzable esters thereof.

9. 16-Deacetoxy-16β-isopropylsulfinylfusidic acid and its $C_{24-25}$-dihydro analogue, and non-toxic pharmaceutically acceptable salts and easily hydrolyzable esters thereof.

10. 11-Keto-16-deacetoxy-16β-isopropylthiofusidic acid, and its $C_{24-25}$-dihydro analogue, and non-toxic pharmaceutically acceptable salts and easily hydrolyzable esters thereof.

11. 3-Keto-16-deacetoxy-16β-isopropylthiofusidic acid, and its $C_{24-25}$-dihydro analogue and non-toxic pharmaceutically acceptable salts and easily hydrolyzable esters thereof.

12. 16-Deacetoxy-16β-ethoxyfusidic acid and its 11-keto analogue, and non-toxic pharmaceutically acceptable salts and easily hydrolyzable esters thereof.

13. 16-Deacetoxy-16β-(2'-fluoroethoxy)fusidic acid and its 11-keto analogue, and non toxic pharmaceutically acceptable salts and easily hydrolyzable esters thereof.

14. 16-Deacetoxy-16β-(2',2',2'-trifluoroethoxy)fusidic acid and its 11-keto analogue, and non-toxic pharmaceutically acceptable salts and easily hydrolyzable esters thereof.

15. 16-Deacetoxy-16β-(1',3'-difluoroisopropyloxy) fusidic acid and non-toxic pharmaceutically acceptable salts and easily hydrolyzable esters thereof.

16. A method for the preparation of a compound of formula I

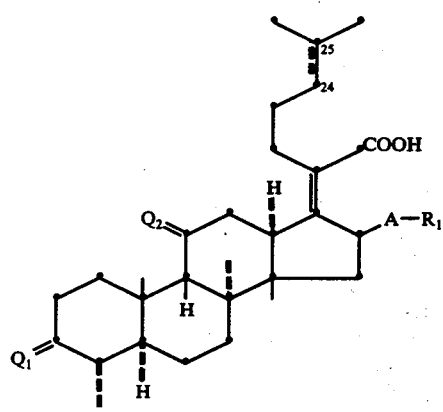

I in which the $C_{24-25}$ bond is a single or a double bond, and in which $Q_1$ and $Q_2$ stand for

or oxygen; A stands for oxygen, sulphur or a sulfinyl radical; $R_1$ stands for a straight or branched alkyl radical having from 1 to 8 carbon atoms, an alkenyl or alkynyl radical having from 2 to 6 carbon atoms, a cycloalkyl radical having from 3 to 7 carbon atoms in the alicyclic ring, an aryl, aralkyl or heterocyclylalkyl radical, or a heterocyclic radical having 5 or 6 ring atoms and containing oxygen, sulphur or nitrogen atoms, all $R_1$ radicals being optionally substituted; and pharmaceutically acceptable salts and easily hydrolyzable esters thereof comprising reacting a compound of formula V$b$

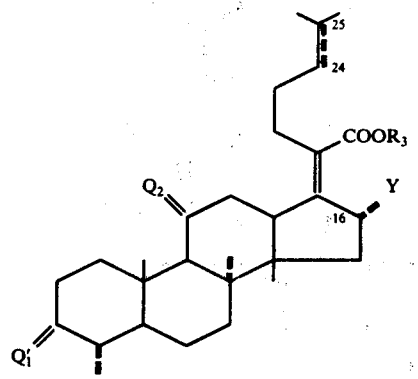

Vb in which $Q_1'$ is $Q_1$ or

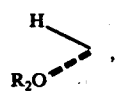

$R_2$ being an alkanoyl, an aralkanoyl or an aroyl radical; $Q_2$ is as defined above; Y stands for chlorine, bromine or iodine; and $R_3$ stands for a straight or branched alkyl radical having from 1 to 6 carbon atoms, an aralkyl radical an alkanoyl- or aroylmethyl radical, an alkanoyl- or aroyl-oxyalkyl radical, an alkyloxymethyl or a cyanomethyl radical; with a compound of formula VII: $R_1$-A-H, in which $R_1$ is as defined above and A represents oxygen or sulphur, yielding a compound of formula VIII:

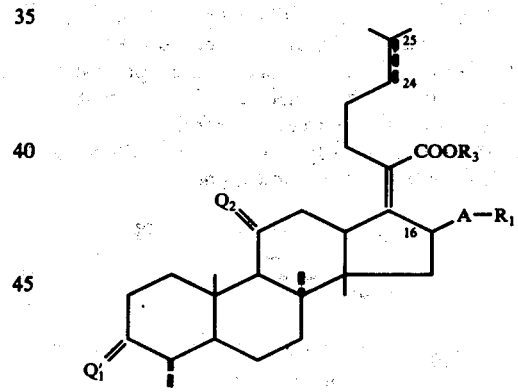

VIII in which $Q_1'$, $Q_2$, $R_1$ and $R_3$ are as defined above, and A is oxygen or sulphur, which compound is thereafter subjected to a hydrolysis, if desired, and a compound of formula I, A being sulphur, optionally is oxidized to a compound of formula I, A being a sulfinyl radical; and the free acid can be transformed into a pharmaceutically acceptable salt or an easily hydrolyzable ester thereof.

17. A method according to claim 16, in which a compound of formula I, wherein $Q_1$ and/or $Q_2$ are

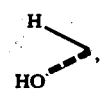

is oxidized to a compound of formula I wherein $Q_1$ and/or $Q_2$ are oxygen.

18. A method according to claim 16 in which a compound of formula I, having a double bond between C-24 and C-25, is converted to a compound of formula I having a single bond between C-24 and C-25 by catalytic hydrogenation.

19. A method for the preparation of a compound of formula I as shown in claim 16 in which $R_1$ stands for an aroyl radical and A is sulphur, comprising reacting a compound of formula IV,

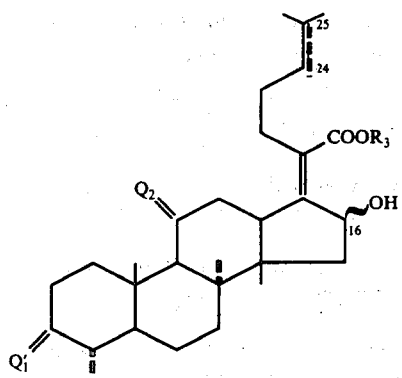

IV in which $Q_1'$, $Q_2$ and $R_3$ are as defined in claim 16, and the OH group at C-16 is α-oriented, with $R_1SSR_1$, thereby obtaining a compound of formula VIII shown in claim 16, in which A is sulphur and $R_1$ is aroyl and $Q_1'$, $Q_2$ and $R_3$ are as defined in claim 16, which compound is thereafter transformed into a compound of formula I as claimed in claim 16.

20. A method for the preparation of compounds of formula I as shown in claim 16, comprising reacting a compound of formula IV, in which the hydroxyl group at C-16 is α-oriented and $Q_1'$ is different from the group

is reacted with a reactive derivative of an alkylsulphonic or arylsulphonic acid, to form a compound of the general formula IX:

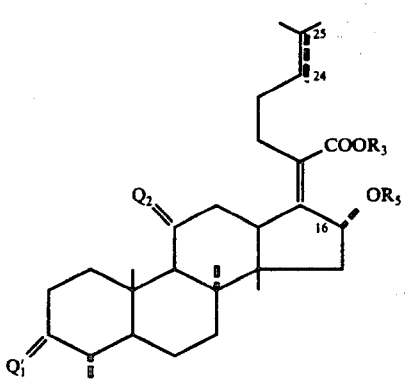

IX in which $Q_2$, $R_3$ and the dotted line between C-24 and C-25 have the meaning as defined above, $Q_1'$ stands for oxygen or the group

$R_2$ being an alkanoyl, aralkanoyl or aroyl radical, and $R_5$ represents an alkylsulphonyl or arylsulphonyl radical, which compound is reacted with a compound $R_1$-A-H, $R_1$ being as defined in claim 16 and A being oxygen or sulphur to form a compound of formula VIII, which compound is thereafter transformed into a compound of formula I as claimed in claim 16.

21. A method according to claim 16 where a compound of formula VIII in which $Q_1'$ and $Q_2$ stand for the group

or oxygen, and $R_3$ represents an unsubstituted or substituted benzyl radical, a cyanomethyl, alkanoylmethyl or aroylmethyl radical is converted into a compound of formula I by hydrogenation.

22. A method according to claim 16 comprising converting a compound of formula VIII in which $Q_1'$, $Q_2$, $R_3$, and the dotted line between C-24 and C-25 have the meaning as defined above, A is oxygen, sulphur or a sulfinyl radical, and $R_1$ stands for a hydroxy-substituted alkyl radical, into a corresponding compound in which $R_1$ stands for a halo-substituted alkyl radical by treatment with halogenating agents, thereafter reacting the halo-substituted alkyl derivative of formula VIII with an aliphatic or aromatic alcohol, with an aliphatic or aromatic mercaptan, with ammonia or an aliphatic or aromatic amine, or with salts of lower alkanoic acids or benzoic acid, with silver or sodium fluoride, alkalimetal azides, nitrites, cyanides or thiocyanates, or with salts of lower thioalkanoic acids or thiobenzoic acid forming a compound of formula VIII in which $Q_1'$, $Q_2$, $R_3$, A, and the dotted line between C-24 and C-25 have the meaning as defined above, and $R_1$ stands for an alkyl radical substituted by a fluorine atom, an alkyloxy, aralkyloxy, aryloxy, alkylthio, aralkylthio, arylthio, amino, alkylamino, dialkylamino, azido, nitro, cyano, thiocyano, alkanoyloxy, aralkanoyloxy, aroyloxy, alkanoylthio or aroylthio radical, which compound is thereafter transformed into a compound of formula I as claimed in claim 16.

23. A pharmaceutical composition containing as the active ingredient a compound of claim 1.

24. A pharmaceutical composition in dosage unit from for systemic treatment of bacterial infections in patients which comprises as a therapeutical ingredient at least one compound of claim 1, the therapeutically active compound being admixed with an atoxic, pharmaceutically acceptable carrier, and the dosage unit being between 100 to 1000 mg, preferably 100 to 500 mg, calculated as the free acid of the therapeutically active compound.

25. A pharmaceutical composition in dosage unit form for topical treatment of bacterial infections in patients which comprise as a therapeutical ingredient at least one compound of claim 1, the therapeutically active compound being admixed with an atoxic, pharmaceutically acceptable carrier, and the dosage unit being between 0.1 mg to 10 mg per sq. centimeter of the infected area.

26. A pharmaceutical composition as claimed in claim 24 wherein the dosage unit is in the form of tablets.

27. A pharmaceutical composition as claimed in claim 24 wherein the dosage unit is in the form of capsules.

28. A pharmaceutical composition as claimed in claim 25 wherein the dosage unit is in the form of a cream.

29. A pharmaceutical composition as claimed in claim 25 wherein the dosage unit is in the form of an ointment.

30. A pharmaceutical composition as claimed in claim 24 wherein the dosage unit is in the injectable form of preparation and contains from 50 to 500 mg, calculated as the free acid, of the therapeutically active compound.

31. A pharmaceutical composition as claimed in claim 24 wherein the dosage unit is a suspension for oral use and containing the therapeutically active compound in an amount of from 2 25 percent.

32. A pharmaceutical composition according to claim 23 in which the active ingredient is one of the compounds claimed in claim 8.

33. A pharmaceutical composition which comprises as the therapeutic ingredient a mixture of a compound of claim 1 and a corticosteroid selected from the group consisting of hydrocortisone, triamcinolone and fluocinolone.

34. A pharmaceutical composition according to claim 25, which comprises as the therapeutic ingredient a mixture of a compound of claim 1 and tetracycline.

35. A pharmaceutical composition according to claim 24, which comprises as the therapeutic ingredient a mixture of a compound of claim 1 and an antibiotic selected from the group consisting of penicillins, cephalosporins, rifamycin, erythromycin, lincomycin and clindamycin.

36. A method of treating bacterial infections which comprises administering into the body a member of the compounds of claim 1.

37. A method according to claim 36 in which the therapeutically active compound is administered by the oral route, in amounts from 200 to 4000 mg per day, preferably from 500 to 2000 mg per day.

38. A pharmaceutical composition in which the active ingredient is one of the compounds claimed in claim 9.

39. A pharmaceutical composition in which the active ingredient is one of the compounds claimed in claim 10.

40. A pharmaceutical composition in which the active ingredient is one of the compounds claimed in claim 11.

41. A pharmaceutical composition in which the active ingredient is one of the compounds claimed in claim 12.

42. A pharmaceutical composition in which the active ingredient is one of the compounds claimed in claim 13.

43. A pharmaceutical composition in which the active ingredient is one of the compounds claimed in claim 14.

44. A pharmaceutical composition in which the active ingredient is one of the compounds claimed in claim 15.

45. A method according to claim 21 wherein a compound of formula VIII in which $R_3$ represents a substituted or unsubstituted benzyl radical or a cyanomethyl radical is converted to a compound of formula I by catalytic hydrogenation.

46. A method according to claim 21 wherein a compound of formula VIII in which $R_3$ represents an alkanoylmethyl or aroylmethyl radical is converted to a compound of formula I by hydrogenation with nascent hydrogen.

* * * * *

UNITED STATES PATENT OFFICE
CERTIFICATE OF CORRECTION

Patent No. 4,060,606            Dated November 29, 1977

Inventor(s) Welf von Daehne and Poul Rodbroe Rasmussen

It is certified that error appears in the above-identified patent and that said Letters Patent are hereby corrected as shown below:

In the heading:

"Daehne et al." should read --von Daehne et al.--

[73] Assignee should read--

Leo Pharmaceutical Products Ltd. A/S (Løvens kemiske Fabrik Produktionsaktieselskab)

Ballerup, Denmark--

[30] Foreign Application Priority Data

June 25, 1975        United Kingdom.....26989/75
November 7, 1975     United Kingdom.....46229/75

Claim 1, line 8;    "alkyclic" should read --alicyclic--

Signed and Sealed this

Ninth Day of May 1978

[SEAL]

Attest:

RUTH C. MASON          LUTRELLE F. PARKER
Attesting Officer       Acting Commissioner of Patents and Trademarks